US009542744B2

(12) United States Patent
Izumo et al.

(10) Patent No.: US 9,542,744 B2
(45) Date of Patent: Jan. 10, 2017

(54) MEDICAL IMAGE DISPLAY APPARATUS AND MEDICAL IMAGE DISPLAY METHOD

(71) Applicant: HITACHI, LTD., Tokyo (JP)

(72) Inventors: Hirohisa Izumo, Tokyo (JP); Kentaro Takahashi, Tokyo (JP); Takayuki Kadomura, Tokyo (JP)

(73) Assignee: HITACHI, LTD., Tokyo (JP)

( * ) Notice: Subject to any disclaimer, the term of this patent is extended or adjusted under 35 U.S.C. 154(b) by 78 days.

(21) Appl. No.: 14/376,522

(22) PCT Filed: Feb. 27, 2013

(86) PCT No.: PCT/JP2013/055074
§ 371 (c)(1),
(2) Date: Aug. 4, 2014

(87) PCT Pub. No.: WO2013/129448
PCT Pub. Date: Sep. 6, 2013

(65) Prior Publication Data
US 2015/0015572 A1 Jan. 15, 2015

(30) Foreign Application Priority Data
Mar. 1, 2012 (JP) ................................. 2012-045211

(51) Int. Cl.
G06T 7/00 (2006.01)
G06T 19/00 (2011.01)
(Continued)

(52) U.S. Cl.
CPC .............. G06T 7/004 (2013.01); A61B 5/055 (2013.01); A61B 5/743 (2013.01); A61B 5/748 (2013.01);
(Continued)

(58) Field of Classification Search
CPC ....... A61B 5/748; A61B 5/7445; A61B 6/463; A61B 2576/023; G06T 7/0012; G06T 2207/10076; G06T 2207/30048; G06T 2219/008; G06F 2203/04802
See application file for complete search history.

(56) References Cited

U.S. PATENT DOCUMENTS 5,528,259 A 6/1996 Bates et al.
6,175,655 B1 1/2001 George, III et al.
(Continued)

FOREIGN PATENT DOCUMENTS

JP 6-203136 7/1994
JP 2001-137231 5/2001
(Continued)

OTHER PUBLICATIONS

International Search Report in PCT/JP2013/055074.

Primary Examiner — Joni Richer
Assistant Examiner — Grace Q Li
(74) Attorney, Agent, or Firm — Cooper & Dunham LLP

(57) ABSTRACT

To retrieve a desired image from plural types of successive images arranged based on various physical quantities, a cuboid object that is an assembly of multiple unit cells is displayed on a display device, a successive image group is arranged according to the physical quantities of the three axes of the cuboid object that are respectively the body-axis direction position, the first time phase intervals, and the second time phase intervals narrower than the first time phase intervals, and the respective images included in the successive image group and the respective unit cells are associated on one-to-one basis and stored in a main memory. When a three-dimensional position in the cuboid object is input by a mouse operation etc., the CPU retrieves one or multiple images associated with one or multiple unit cells
(Continued)

determined according to the input three-dimensional position from the main memory and displays the images in an image display region.

11 Claims, 26 Drawing Sheets

(51) Int. Cl.
| | |
|---|---|
| *G06F 3/0481* | (2013.01) |
| *G06F 3/0484* | (2013.01) |
| *A61B 5/055* | (2006.01) |
| *A61B 5/00* | (2006.01) |
| *A61B 6/00* | (2006.01) |
| *A61B 6/03* | (2006.01) |
| *G01R 33/56* | (2006.01) |

(52) U.S. Cl.
CPC ....... *G06F 3/04815* (2013.01); *G06F 3/04845* (2013.01); *G06T 7/0012* (2013.01); *G06T 19/00* (2013.01); *A61B 5/7425* (2013.01); *A61B 6/032* (2013.01); *A61B 6/463* (2013.01); *A61B 6/5288* (2013.01); *A61B 2576/023* (2013.01); *G01R 33/5608* (2013.01); *G06F 2203/04802* (2013.01); *G06T 2207/10081* (2013.01); *G06T 2207/10088* (2013.01); *G06T 2207/30004* (2013.01); *G06T 2219/008* (2013.01)

(56) References Cited

U.S. PATENT DOCUMENTS

| | | | | |
|---|---|---|---|---|
| 6,831,646 | B1* | 12/2004 | Cottrille | G06T 11/206 |
| | | | | 345/473 |
| 2003/0035584 | A1* | 2/2003 | Nicolas | G06F 19/321 |
| | | | | 382/232 |
| 2005/0184988 | A1* | 8/2005 | Yanof | G06T 15/08 |
| | | | | 345/424 |
| 2008/0033312 | A1* | 2/2008 | Nakai | A61B 5/04007 |
| | | | | 600/509 |
| 2009/0060309 | A1 | 3/2009 | Tsujii et al. | |
| 2011/0103664 | A1* | 5/2011 | Kovalski | G06T 7/0028 |
| | | | | 382/131 |
| 2011/0286647 | A1* | 11/2011 | Cao | G06F 3/04815 |
| | | | | 382/131 |
| 2012/0245453 | A1* | 9/2012 | Tryggestad | A61B 6/463 |
| | | | | 600/413 |

FOREIGN PATENT DOCUMENTS

| | | |
|---|---|---|
| JP | 2003-325514 | 11/2003 |
| JP | 2009-56032 | 3/2009 |

* cited by examiner

FIG.6
(A) SPECIFY WITH MOUSE POINTER
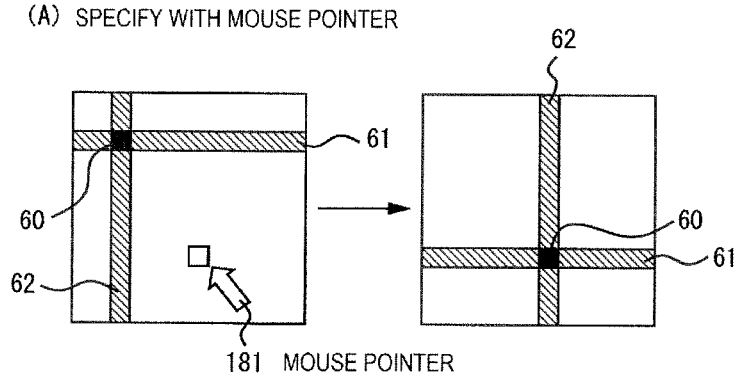
(B) MOVE COLUMN LINE
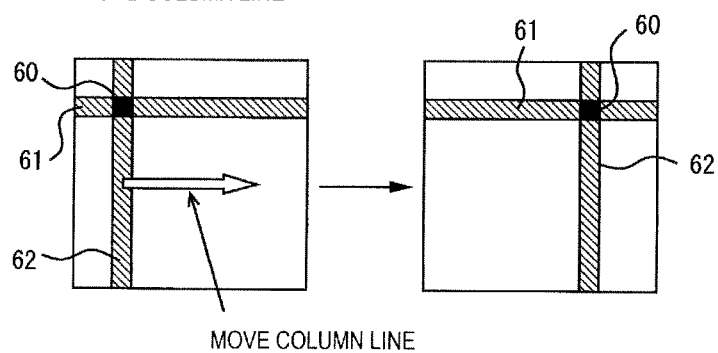

FIG.16
(A)
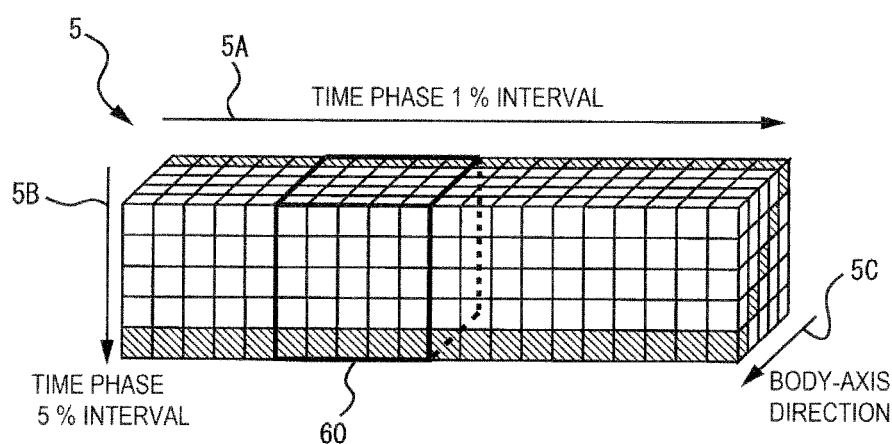
(B)
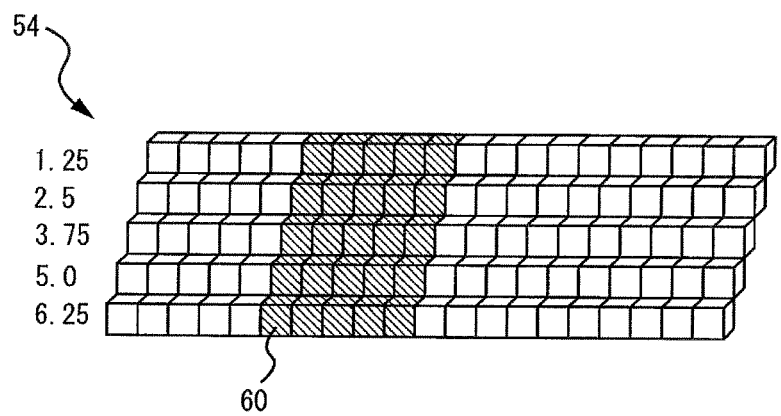

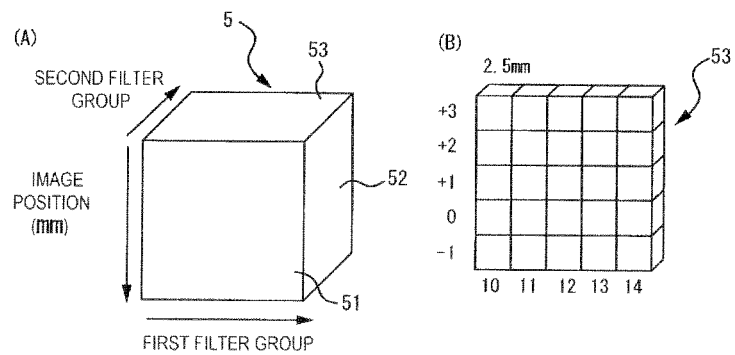
FIG.21
10:HEAD/SMOOTH 2
11:HEAD/SMOOTH 1
12:HEAD/STANDARD
13:HEAD/SHARP 1
14:HEAD/SHARP 2
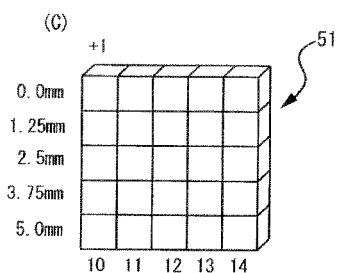
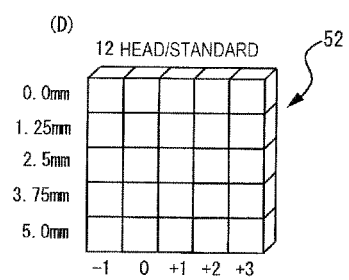

FIG.25
(A)
(EX.) IF IMAGE THICKNESS IS DIFFERENT
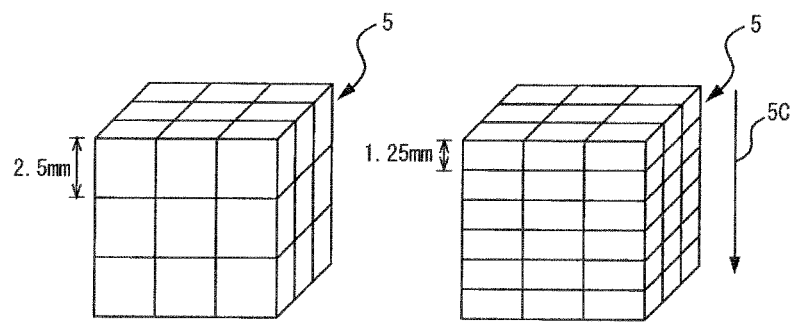
(B)
(EX.) IF NUMBER OF IMAGES IS DIFFERENT
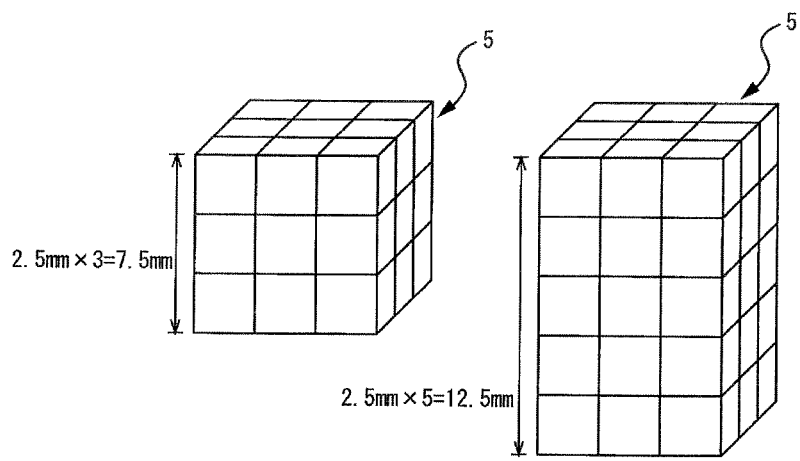

FIG. 26
(A)
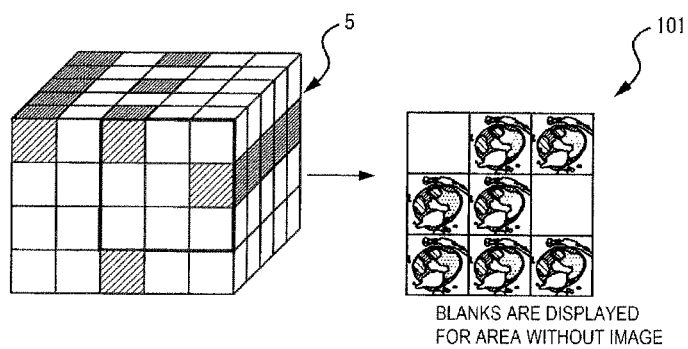
BLANKS ARE DISPLAYED
FOR AREA WITHOUT IMAGE
(B)
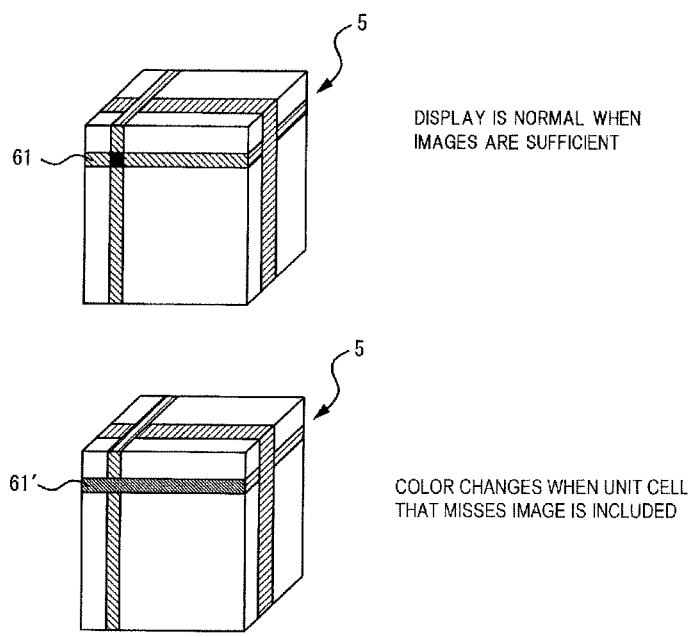
DISPLAY IS NORMAL WHEN
IMAGES ARE SUFFICIENT
COLOR CHANGES WHEN UNIT CELL
THAT MISSES IMAGE IS INCLUDED

MEDICAL IMAGE DISPLAY APPARATUS AND MEDICAL IMAGE DISPLAY METHOD

TECHNICAL FIELD

The present invention relates to a medical image display device and a medical image display method, and in particular, to a technique for user support functions suitable for displaying successive images and retrieving an image.

BACKGROUND ART

Conventionally, medical image diagnoses have been performed using medical images from an X-ray CT (Computed Tomography) apparatus, an MRI (Magnetic Resonance Imaging) apparatus, etc. Recently, the number of images that can be obtained by scanning once has been increased in accordance with the body-axis direction of a detector in a medical image display device getting multi-row. In order to observe such a vast number of image groups efficiently, for example, an image display device as described in PTL 1 and 2 is proposed.

In PTL 1, an image display device having a coordinate display unit with matrix form that shows series data in rows and successive images in columns so that series data and images successive in the body-axis direction can be easily specified is described. Then, the number of images to be displayed etc. can be specified by placing a cursor on the coordinate display unit to display an image on which the cursor is placed and by zooming in/out the cursor.

Also, in PTL 2, an image display method considering position information of an image and thickness in the body-axis direction, an image display method according to how to select an image, etc. are described. According to such medical image display devices described in PTL 1 and 2, successive images can be two-dimensionally displayed using two axes such as a series data axis and a body-axis direction axis.

CITATION LIST

Patent Literature

PTL 1: Japanese Unexamined Patent Application Publication No. 2003-150138
PTL 2: Japanese Unexamined Patent Application Publication No. 2005-160503

SUMMARY OF INVENTION

Technical Problem

However, even if the medical image display devices described in PTL 1 and 2 above are used, displaying operations of numerous steps had to be performed in order to find out a target image from many kinds of images.

For example, a parameter referred to as "R-R time phase" is specified for the reconstruction in cardiac-gated scanning and reconstruction processes. The R-R time phase is a parameter to specify at what percentage the reconstruction process is performed for projection data collected from an R wave based on the R wave of an electrocardiogram. In order to determine an optimal R-R time phase, for example, in case of an expansion phase, an operator generally (1) first reconstructs 30 time phases from time phase 70% to 99% at 1% intervals, (2) begins to find a stable time phase for the right coronary artery from the reconstructed images at 5% intervals, (3) and then determines a most stable time phase of the surrounding time phases for the right coronary artery at 1% intervals. (4) Then, a diagnostic image is reconstructed using the parameter required for a diagnosis in the determined phase.

If such optimal phase selection is performed using an image selecting unit of two axes used in conventional image display devices or a method to select a desired image from an image group displayed in matrix form, the above (2) and (3) processes of two steps needs to be performed for a plurality of body-axis direction positions. Therefore, it takes a very long time to perform the steps. This tendency becomes conspicuous as the number of images increases. Therefore, it is hoped that a desired image can be retrieved more efficiently. In case of the above example, if there is a system where a body-axis direction position can be freely changed and observed while checking successive images aligned at loose time phase intervals and those aligned at tight time phase intervals simultaneously for example, an optimal phase can be found efficiently.

The present invention was made in light of the problem described before, and the purpose is to provide a medical image display device and a medical image display method appropriate to retrieve a desired image from plural kinds of successive images aligned based on various physical quantities.

Solution to Problem

In order to achieve the purpose described before, the first invention is a medical image display device that displays medical images and that is comprised of a display unit displaying a cuboid object that is an assembly of multiple unit cells, a storage unit memorizing the respective images included in a successive image group and the respective unit cells with them associated on one-to-one basis by respectively associating the successive image group of the medical images arranged successively according to predetermined physical quantities for the respective three directions of the three axes of the cuboid object, an input unit inputting a three-dimensional position in the cuboid object, and a control unit controlling so that one or multiple images associated with one or multiple unit cells determined according to the three-dimensional position input from the input unit are retrieved from the storage unit and are displayed on the display unit.

Also, the second invention is a medical image display method that a medical image display device displaying medical images performs and includes a displaying step where a display unit displays a cuboid object that is an assembly of multiple unit cells, a memorizing step where a storage unit memorizes the respective images included in a successive image group and the respective unit cells with them associated on one-to-one basis by respectively associating the successive image group of the medical images successively arranged according to a predetermined physical quantities with the respective directions of the three axes of the cuboid object, an inputting step where an input unit inputs a three-dimensional position in the cuboid object, and a controlling step where a control unit controls so that one or multiple images associated with one or multiple unit cells determined according to the three-dimensional position input from the input unit are retrieved from the storage unit and are displayed on the display unit.

Advantageous Effects of Invention

The present invention can provide a medical image display device and a medical image display method appropriate to retrieve a desired image from plural kinds of successive images aligned based on various physical quantities.

BRIEF DESCRIPTION OF DRAWINGS

FIG. 6 is an explanatory diagram of how to specify a three-dimensional position of the cuboid object 5.

FIG. 16 is an explanatory diagram of a three-dimensional position specifying operation when the non-orthogonal cross section 54 is an active surface and for a unit cell to be selected.

FIG. 21 is an example of physical quantities associated with each axis of the cuboid object 5 in a filtering mode.

FIG. 25 is an explanatory diagram of display size modes of the cuboid object 5.

FIG. 26 is a display example of the cuboid object 5 according to the presence or absence of images.

DESCRIPTION OF EMBODIMENTS

Based on the following diagrams, the embodiments of the medical image display device 1 of the present invention will be described in detail.

First Embodiment

First, referring to FIG. 1, the configuration of the medical image display device 1 in the first embodiment will be described.

The medical image display device 1 is a computer that performs processes such as image creation and image analysis and includes the image viewer 100 (FIG. 2) that displays medical images.

Figure 1:
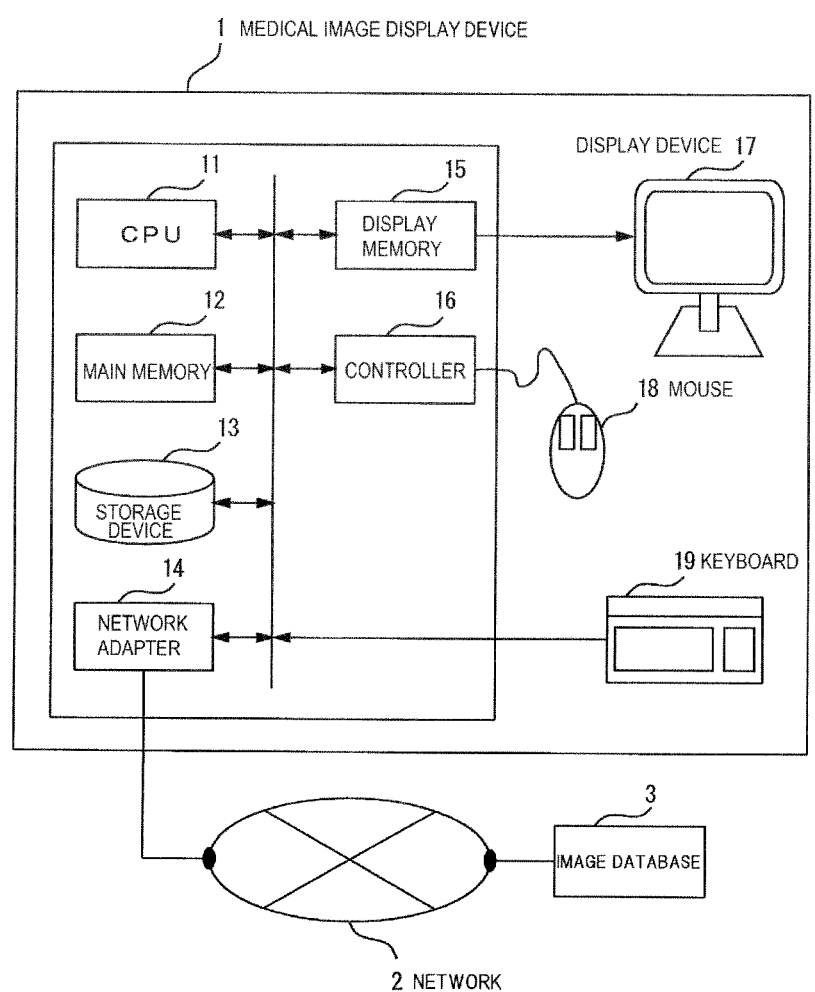
FIG. 1 is an overall configuration diagram of the medical image display device 1.

As shown in FIG. 1, the medical image display device 1 is comprised of the CPU (Central Processing Unit) 11, the main memory 12, the storage device 13, the network adapter 14, display memory 15, the controller 16 that is an interface with external devices such as the mouse 18, the display device 17, and input devices such as the mouse 18 and the keyboard 19, and the respective parts are connected via a bus. Also, the medical image display device 1 may be configured so that it can be connected to the image database 3 via the network 2.

The CPU 11 calls a program stored in the storage device 13 etc. to a work memory region on the RAM of the main memory 12 to execute the program, performs drive control for the respective parts connected via a bus, and achieves various processes that the medical image display device 1 performs. For example, a program for the above image viewer 100 is read from the storage device 13 to execute image display and retrieval processing.

In the present invention, the above image viewer 100 has the cuboid object 5 (see FIGS. 2 and 3) to be described later as a GUI (Graphical user Interface) to select an image to be displayed in the image display region 101. The CPU 11 associates the successive image groups aligned based on different physical quantities respectively with the three axes of the cuboid object 5 and stores the relationship information in the main memory 12. Hence, the respective unit cells 50 of the cuboid object 5 are associated with the respective images included in successive images. Also, the CPU 11 accepts an operation for the cuboid object 5 by an operator, changes a display state of the cuboid object 5 according to the operation contents, and changes a medical image to be displayed in the predetermined image display region 101 of the image viewer 100.

The details for the image viewer 100 and the cuboid object 5 will be described later.

The main memory 12 is comprised of a ROM (Read Only Memory), a RAM (Random Access Memory), etc. The ROM perpetually holds a boot program of a computer, programs such as BIOS, data, etc. Also, the RAM temporarily holds programs, data, etc. loaded from the ROM, the storage device 13, etc. as well as has a work area that the CPU 11 uses to perform various processes.

The storage device 13 is a storage device that reads and writes data to an HDD (Hard Disk Drive) and the other recording media and stores programs that the CPU 11 executes, data required to execute a program, an OS (Operating System), etc. For the programs, a control program equivalent to the OS, an application program, a program to achieve the image viewer 100 of the present invention, etc. are stored. These respective program codes are read and written by the CPU 11 as needed, are transferred to the RAM of the main memory 12, and then are executed as various means.

The network adapter 14 has a communication control device, a communication port, etc. and mediates communication between the medical image display device 1 and the network 2. Also, the network adapter 14 performs communication control with the image database 3, the other computers, or image scanning devices such as an X-ray CT apparatus and an MRI apparatus via the network 2.

The controller 16 is a port to be connected to peripheral devices and sends and receives data with the peripheral devices. For example, a pointing device such as the mouse 18 and a stylus pen may be connected via the controller 16.

The display memory 15 is a buffer that temporarily accumulates display data to be input from the CPU 11. The accumulated display data is output so the display device 17 at a predetermined timing.

The display device 17 is comprised of a display device such as a liquid crystal panel and a CRT monitor and a logic circuit to execute display processes by collaborating with the display device, and is connected to the CPU 11 via the display memory 15. The display device 17 displays display data accumulated in the display memory 15 by control of the CPU 11.

Input devices are the mouse 18, keyboard 19, etc. for example and outputs various commands and information to be input by an operator to the CPU 11. An operator dialogically operates the medical image display device 1 using external devices such as the display device 17, the mouse 18, and the keyboard 19.

The network 2 includes various communication networks such as a LAN (Local Area Network), a WAN (Wide Area Network), the Intranet, and the Internet and mediates communication connection among the image database 3, servers, the other information devices etc. and the medical image display device 1.

The image database 3 accumulates and stores image data scanned by an image scanning device. In FIG. 1, although the image database 3 is configured to be connected to the medical image display device 1 via the network 2, the image database 3 may be disposed in the storage device 13 in the medical image display device 1, for example.

Next, referring to FIGS. 2 to 4, the image viewer 100 and the cuboid object 5 will be described.

As described above, the cuboid object 5 is a GUI provided in the image viewer 100 and supports displaying and retrieving an image.

Figure 2:
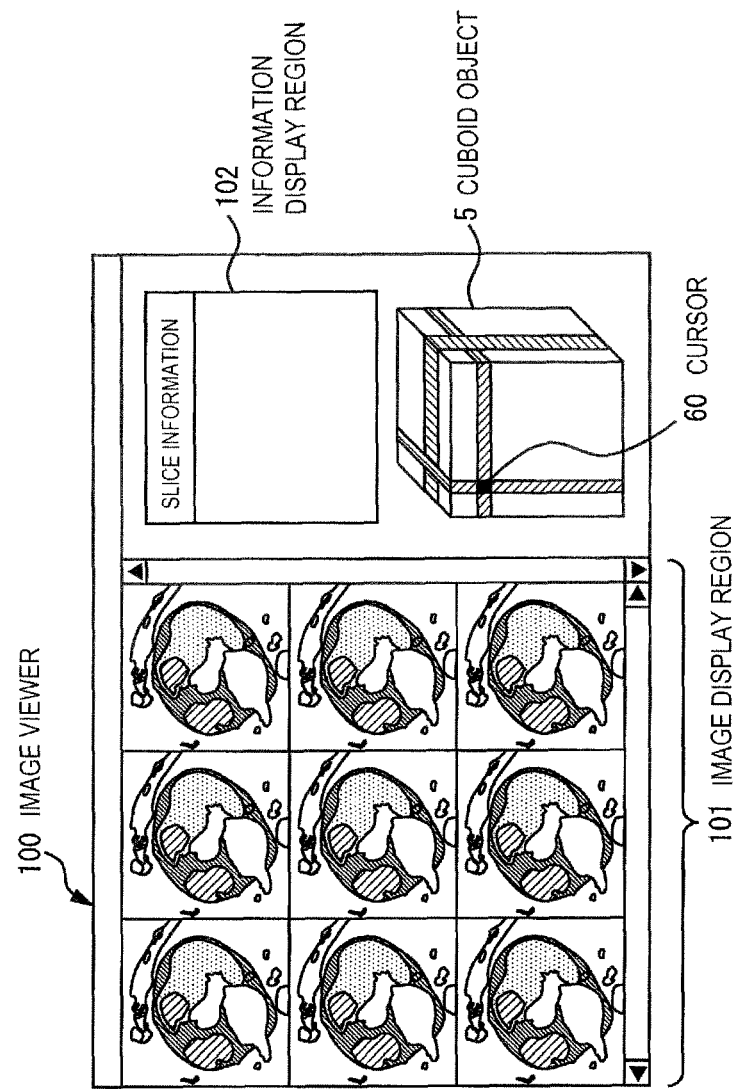
FIG. 2 is an explanatory diagram of the display screen of the image viewer 100.

As shown in FIG. 2, the cuboid object 5 is displayed on the display screen of the image viewer 100, in addition, the image display region 101 that displays one or multiple medical images and the information display region 102 that displays information about the displayed image (object information, detected date and time information, slice information, etc.) are provided.

Figure 3:
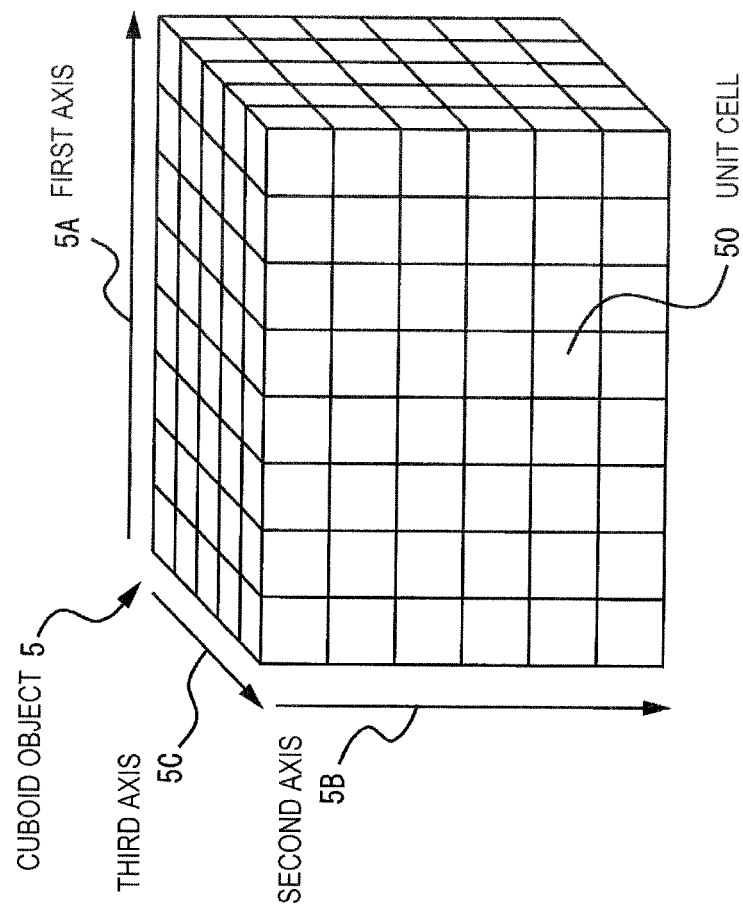
FIG. 3 is a diagram showing an example of the cuboid object 5.

As shown in FIG. 3, the cuboid object is an assembly of a plurality of the unit cells (cubic frames) 50, and the respective unit cells 50 are associated with respective images included in a successive image group on one-to-one basis. The three axes in the vertical, horizontal, and depth directions of the cuboid object 5 are respectively associated with successive image groups of medical images aligned successively according to predetermined physical quantities. The following description will describe a case where the cuboid object 5 is associated with 30 time phases of successive image groups (30 series) reconstruct R-R time phases 70% to 99% at 1% intervals using cardiac-gated scanning as an example.

For the cuboid object 5 in FIG. 3, the first axis 5A is associated with the successive image group of "the first time phase intervals (for example, the time phase 5% intervals)", the second axis 5B is associated with the successive image group of "the body-axis direction position", and the third axis 5C is associated with the successive image group of the physical quantities "the second time phase intervals (for example, the time phase 1% intervals) closer than a time phase associated with the first axis 5A".

Figure 4:
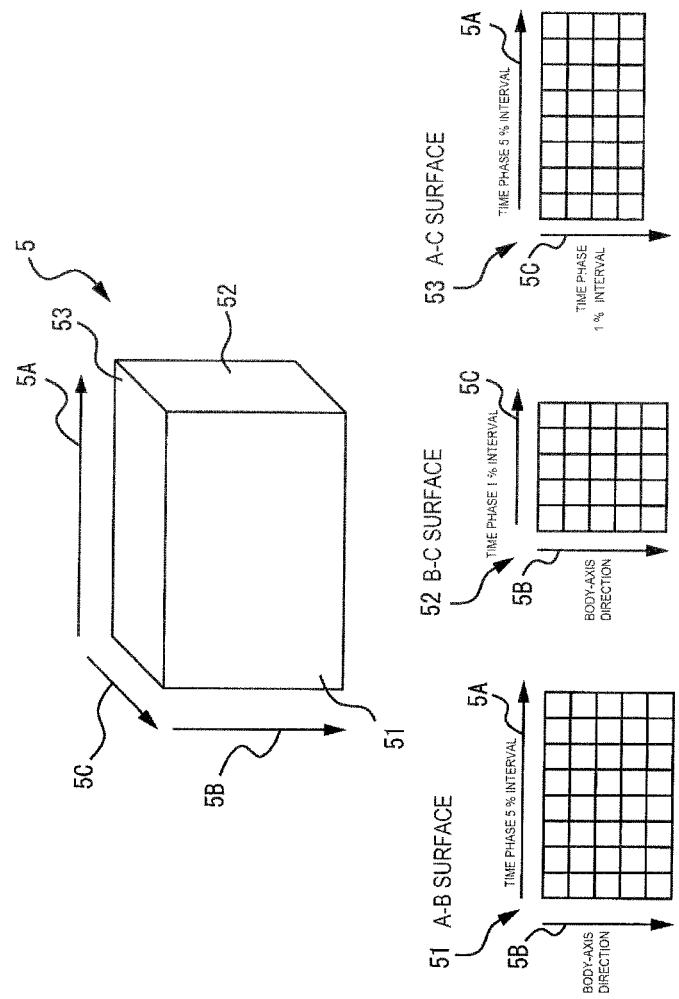
FIG. 4 is a diagram showing an example of a successive image group associated with each surface of the cuboid object 5.

Then, as shown in FIG. 4, on the surface 51 (referred to as the A-B surface 51) that is comprised of the first axis 5A and second axis 5B, successive images that were aligned in the order of the body-axis direction position in the column direction are additionally aligned at time phase 5% intervals in the row direction. Also, on the surface 52 (referred to as the B-C surface 52) that is comprised of the second axis 5B and third axis 5C, successive images that were aligned in the order of the body-axis direction position in the column direction are additionally aligned at time phase 1% intervals in the row direction. Also, on the surface 53 (referred to as the A-C surface 53) that is comprised of the first axis 5A and third axis 5C, images in a body-axis direction position are aligned at time phase 1% intervals in the column direction and at time phase 5% intervals in the row direction.

A state where each axis is associated with physical quantities (successive images) and a state where each unit cell 50 of the cuboid object 5 is associated with each image are stored in the main memory 12.

When an arbitrary three-dimensional position of the cuboid object 5 is specified by an operator, the CPU 11 retrieves each image associated with one or multiple unit cells 50 in a specified three-dimensional position from the main memory 12 and displays the image in the image display region 101. Hence, a desired image can be displayed easily from a plurality of successive image groups.

Next, referring to FIGS. 5 to 11, operations for the cuboid object 5 will be described.

The cuboid object 5 accepts various operations such as specifying a three-dimensional position (moving the cursor 60), changing the size of the cursor 60, changing the number of the cursor 60, changing an active surface, and changing an axis direction. The respective operations are input from input devices such as the mouse 18 and the keyboard 19, and the CPU 11 changes a display state of the cuboid object 5 based on an input signal.

Figure 5:
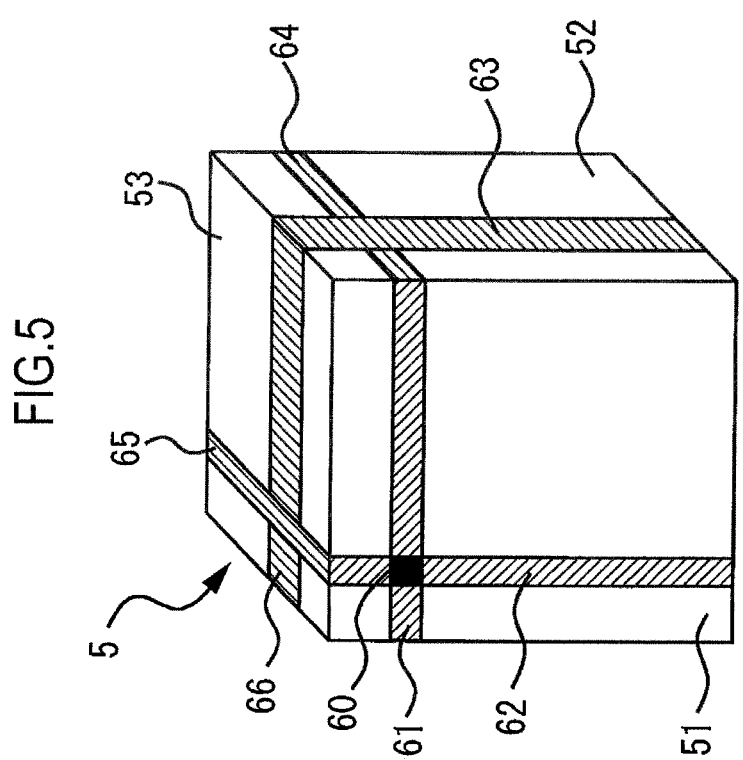
FIG. 5 is an explanatory diagram of the cursor 60 and positioning lines (column lines 62, 63, and 65; row lines 61, 64, and 66) of the cuboid object 5.

As shown in FIG. 5, the cursor 60 to specify a three-dimensional position (the unit cell 50) is displayed on the cuboid object. Also, on the respective surfaces 51, 52, and 53, positioning lines running in the row and column directions from the cursor 60 position are displayed. In the following description, a positioning line running in the row direction is referred to as a row line (the lines 61, 64, and 66 in FIG. 5), and a positioning line running in the column direction is referred to as a column line (the lines 62, 63, and 65 in FIG. 5). On the respective surfaces 51, 52, and 53, the cursor 60 is located at an area where the row line and column line cross. Because the cuboid object 5 is displayed in a perspective diagram as shown in FIG. 5, a cursor position in the depth direction can be checked by referring to a line position displayed on surfaces (the surfaces 52 and 53 in FIG. 5) other than a front surface (the surface 51 in FIG. 5). It is preferable that an area (the cursor 60) where the row line and column line cross is displayed using colors, patterns, blinking, etc, so as to distinguish from the other areas.

When a position of the cursor 60 is specified on the cuboid object 5, an image associated with the unit cell 50 (selected cell) on which the cursor 60 is placed is displayed in the image display region 101 of the image viewer 100 (see FIG. 2).

According to operations of the mouse 18 or the keyboard 19, the cursor 60 moves and is displayed on the respective unit cells 50 in the cuboid object 5. FIG. 6(A) shows an example where the cursor 60 position is directly specified by the mouse 18, and FIG. 6(B) shows an example where a column line is moved from side to side by operating the arrow keys on the keyboard 19 or dragging using the mouse 18. As shown in FIG. 6(A), when the cursor 60 position is directly specified by the mouse pointer 181, the CPU moves and displays the cursor 60 position in a position specified by the mouse pointer 181. Also, as shown in FIG. 6(B), when a column line is moved from side to side by operating the arrow keys on the keyboard 19, the CPU 11 moves the row line 61 according to operations with the "UP" and "DOWN" keys on the keyboard 19 or moves the column line 62 according to operations with the "LEFT" and "RIGHT" keys, and a position where the row line and column line cross is displayed as the position of the cursor 60.

The CPU 11 recognizes the unit cell 50 in a position where the cursor 60 is placed as a selected cell.

Also, the number of the unit cell 50 that the cursor 60 selects collectively may be increased or decreased by accepting changes of the row line and column line widths by an operator. When the row line and column line widths are changed by a predetermined operation with the mouse 18, the keyboard 19, etc., the size of the cursor 60 is changed. That is, all the unit cells 50 included in the cursor 60 region are selected. Hence, a plurality of the unit cells 50 can be selected collectively. For example, if all the line widths of the row lines and column lines of the respective surfaces 51, 52, and 53 are changed to the two-line width, the cursor 60 can select a total of the eight (=2×2×2) unit cells 50.

Additionally, when a plurality of the unit cells 50 are thus selected sterically, the CPU 11 recognizes the unit cell 50 on an active surface (for example, a surface displayed in front (the front surface of a displayed screen)) as a selected cell. Then, an image associated with the selected cell is displayed in the image display region 101. Moreover, the active surface is moved in the depth direction in order by mouse scrolling etc. to be described later, which displays an image associated with the unit cells 50 of the respective surfaces in the depth direction among the unit cells 50 selected by the cursor 60 in the image display region 101 (see FIG. 10).

Figure 7:
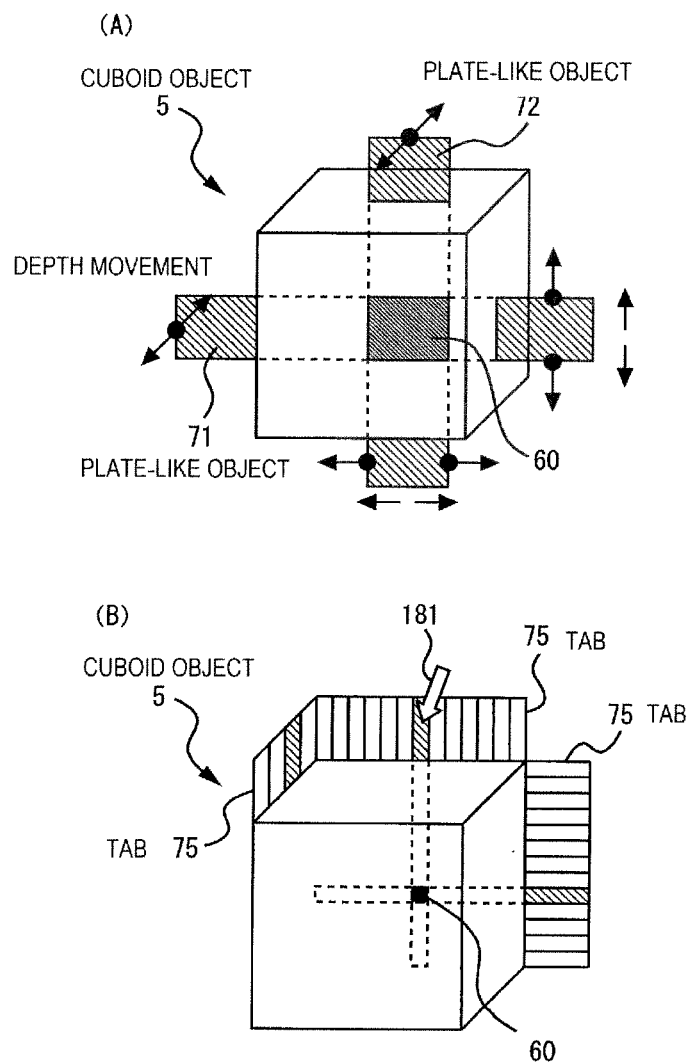
FIG. 7 is an explanatory diagram of how to specify a three-dimensional position of the cuboid object 5.

The other examples for specifying a three-dimensional position are shown in FIG. 7.

FIG. 7(A) shows an example for specifying a three-dimensional position by the plate-like objects 71 and 72. In the example of FIG. 7(A), the CPU 111 displays the cuboid object 5 translucently and displays the two plate-like objects 71 and 72 non-transparently that are orthogonal vertically and horizontally so that they are visible. The crossing area of the plate-like objects 71 and 72 is a position of the cursor 60. The plate-like object 71 that extends horizontally can move in the up-down and depth directions of the cuboid object 5, and the plate-like object 72 that extends vertically can move in the left-right and depth directions of the cuboid object 5. Then, the plate-like objects 71 and 72 is moved by the mouse 18 etc., which moves also the position of the cursor 60. Additionally, the widths of the plate-like objects 71 and 72 can be changed by input commands from the mouse 18 etc. While the operation for specifying a three-dimensional position using a row line and column line in FIG. 5 needs to operate three line objects, the example for the plate-like objects 71 and 72 in FIG. 7(A) is user-friendly because a three dimensional position can be specified by operating the two plate-like objects. Also, because the unit cell 50 of the cuboid object 5 is translucent, the specified three-dimensional position is highly visible.

In FIG. 7(B), the cuboid object 5 is translucent, and the tabs 75 are displayed along the respective axes outside the cuboid object 5. The respective tabs 75 are scaled (1%, 2%, etc. for when an axis shows time phase intervals), and a three-dimensional position of the cursor 60 can be specified by specifying a position for the scales of the tabs 75 of the respective axes using the mouse pointer 181 etc. An example in FIG. 7(B) is user-friendly because a scale of the tabs 75 can be selected directly. Also, the cuboid object 5 is displayed translucently, and the cursor 60 is displayed non-transparently for visibility, which makes the specified three-dimensional position of the cursor 60 highly visible.

Figure 8:
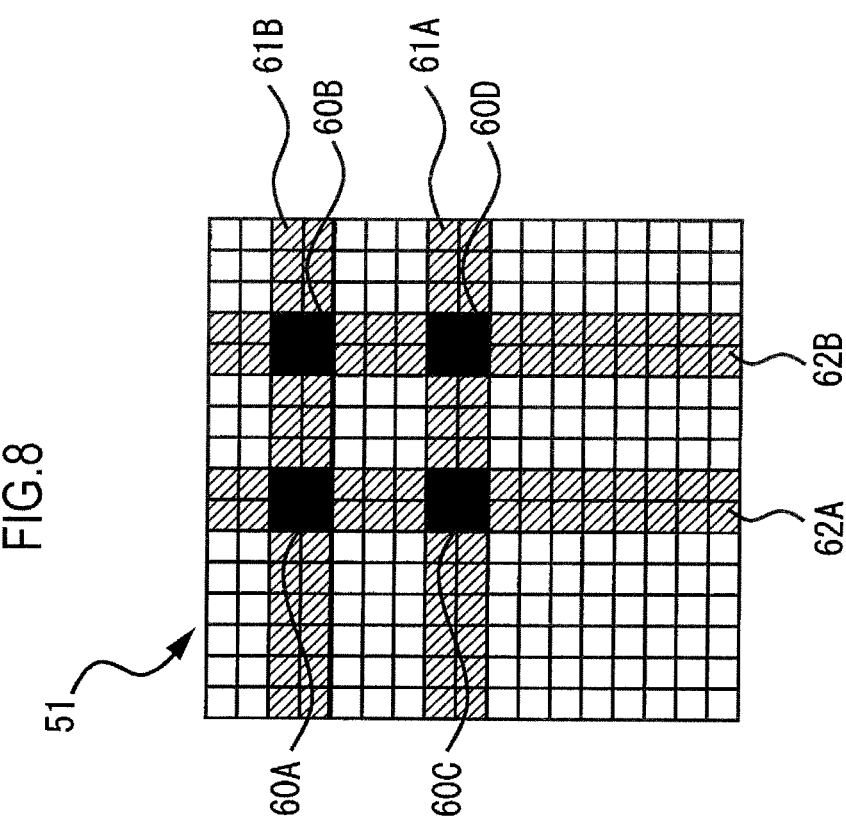
FIG. 8 is an example for when a plurality of positioning lines are provided for in a column or row direction.

Additionally, as shown in FIG. 8, a plurality of positioning lines (column lines and row lines) may be provided on a surface. In the example of FIG. 8, a case where the two column lines 62A and 62B as well as the two row lines 61A and 61B are provided on the surface 51 of the cuboid object 5 is shown. In this case, the four regions where the respective lines cross are the cursors 60A, 60B, 60C, and 60D. In the example of FIG. 8, because the widths of the respective lines are the same as those of two unit cells if a line in the depth direction is one line, the cursors 60A, 60B, 60C, and 60D include the four unit cells 50 respectively, and a total of the 16 unit cells 50 are to be selected. The CPU 11 displays a total of 16 images associated with the four unit cells 50 included in the four cursors 60A, 60B, 60C, and 60D respectively in the image display region 101.

The active surface is a selected surface of a plurality of the unit cells 50 selected (may be selected sterically) by the cursor 60. For example, the surface may be the one displayed on the most-front surface, the one selected out of surfaces parallel to the front surface, or the one set as an active surface in advance.

Figure 9:
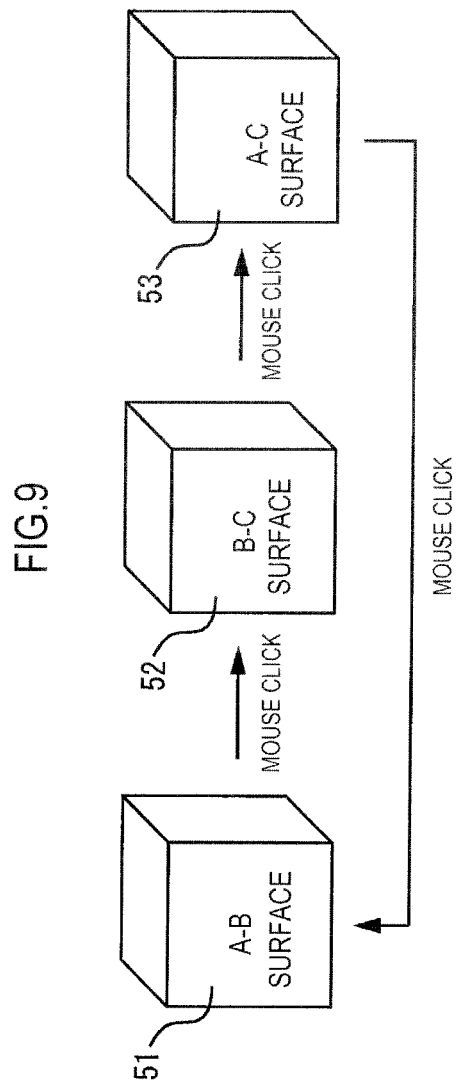
FIG. 9 is an explanatory diagram of an operation to change a front surface (active surface) of the cuboid object 5.

The CPU 11 accepts an operation to switch an active surface. As shown in FIG. 9 for example, the cuboid object 5 is rotated each time a click is performed using the mouse 18 in order to sequentially switch a surface displayed on the front surface, which changes the active surface.

Figure 10:
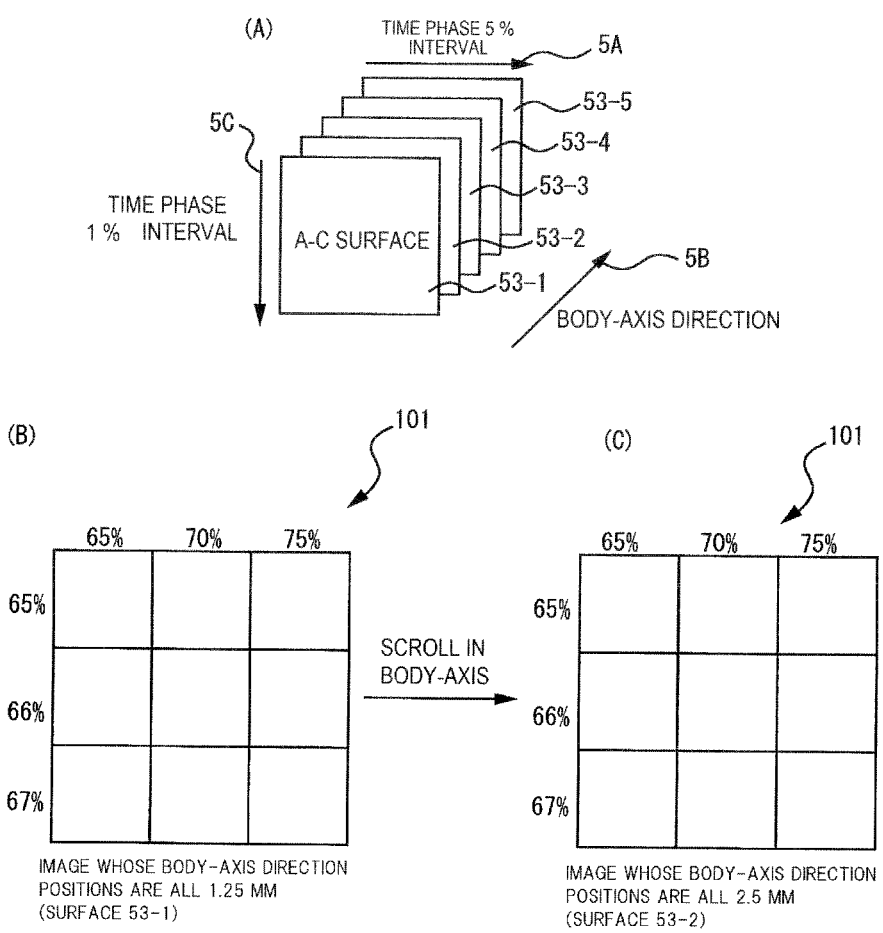
FIG. 10 is an explanatory diagram of an operation to move an active surface in a depth direction of the cuboid object 5.

Also for example, a case where an active surface can be moved in the depth direction of the cuboid object 5 by operations such as rotating the wheel of the mouse 18 may be configured. The example of FIG. 10 shows that the most-front surface is an active surface in an early stage in a case where the front surface of the cuboid object 5 (the front surface of the displayed screen) is the A-C surface 53 and shows that the active surface is sequentially moved in the axis 5B direction (depth direction) by rotating the mouse wheel.

As shown in FIG. 10(A) for example, when the A-C surface 53-1 is displayed as an active surface on the most-front surface, images of the same body-axis direction position (for example, the body-axis direction position is 1.25 mm) are displayed as shown in FIG. 10(B) at the time phase 5% intervals (65%, 70%, and 75%) in a horizontal direction and at the time phase 1% intervals (65%, 66%, and 67%) in a vertical direction in the image display region 101. When the cursor 60 is moved in the depth direction of the cuboid object 5 by operating the mouse wheel in this state, as shown in FIG. 10(C), the active surface is switched to the surface 53-2, which is to display images of the body-axis direction position 2.5 mm at the time phase 5% intervals (65%, 70%, and 75%) in a horizontal direction and at the time phase 1% intervals (65%, 66%, and 67%) in a vertical direction.

Figure 11:
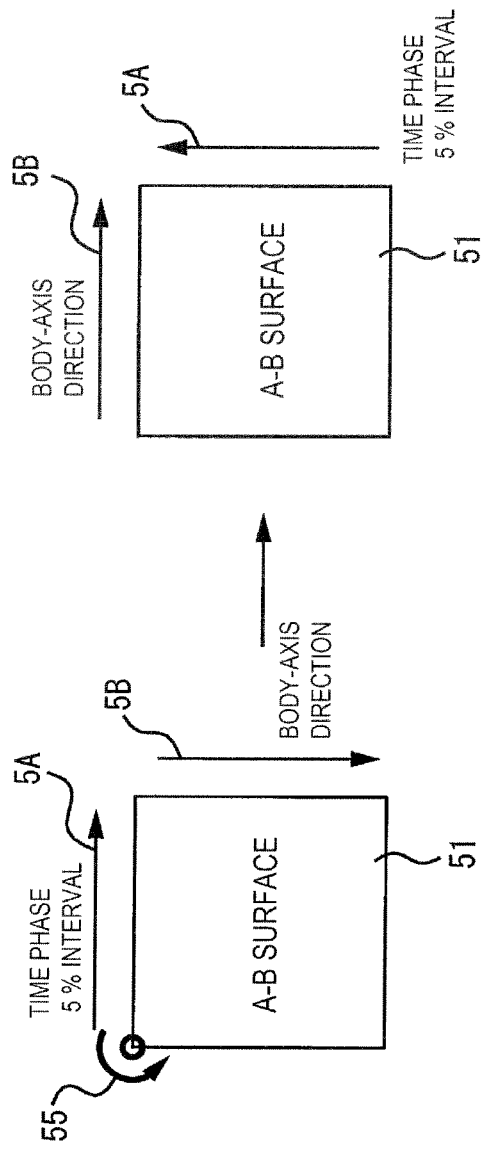
FIG. 11 is an explanatory diagram of an operation to change an axis orientation.

Additionally, as shown in FIG. 11, a case where only the axis orientation can be rotated without changing an active surface may be configured. The CPU 11, for example, displays the axis direction rotation GUI 55 in a corner or vicinity of the cuboid object 5, and when the axis direction rotation GUI 55, for example, is rotated by operations such as mouse dragging, vertical and horizontal axes alternate with each other. Images displayed in the image display region 101 are also rearranged according to the axis orientation.

Figure 12:
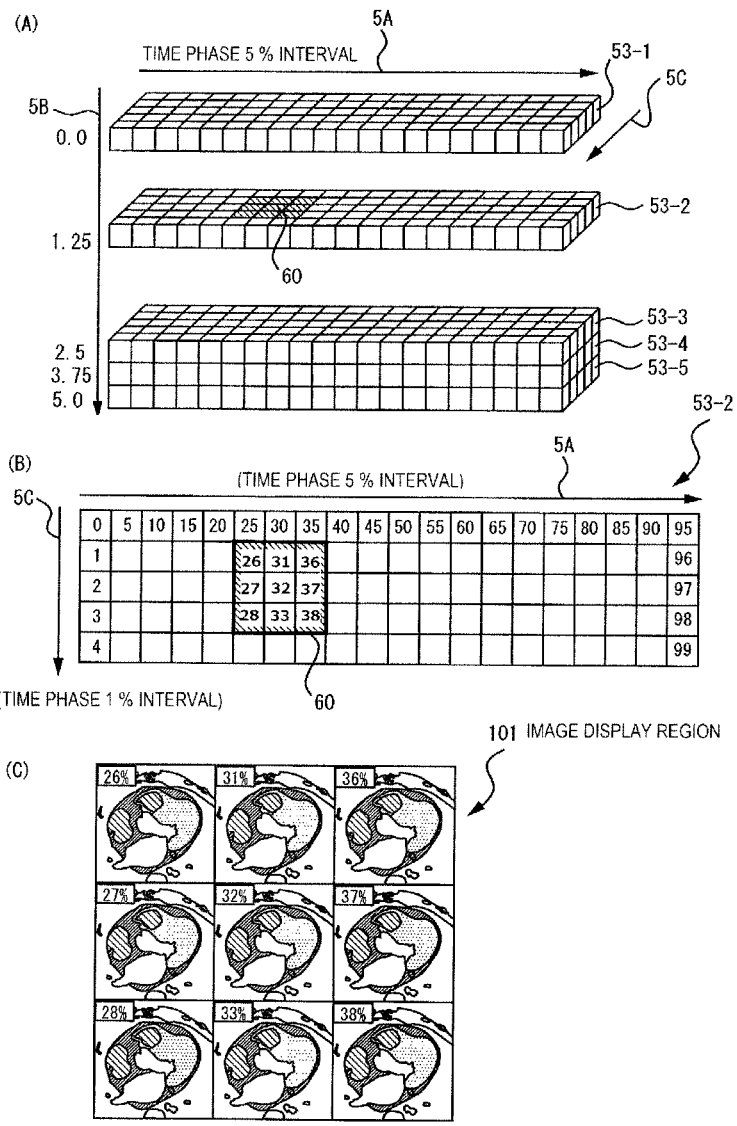
FIG. 12 is an image display example for when an orthogonal cross section (the surface 53-2) of the cuboid object 5 is an active surface.

Next, referring to FIG. 12, the relationship between specifying a three-dimensional position in the cuboid object 5 and an image displayed in the image display region 101 will be described.

In FIG. 12(A), the cuboid object 5 is separated for detailed description and shown with the first axis 5A as the first time phase intervals (by 5%), the second axis 5B as the body-axis direction position (by 1.25 mm), and the third axis 5C as the second time phase intervals (by 1%). As shown in FIG. 12(B), the cursor 60 is to be moved to the position that includes the nine unit cells 50 surrounding the center cell in the second from the top (body-axis direction position 1.25 mm), the seventh from the left, and the third from the near side (time phase 32%). That is, the A-C surface 53-2 in the second from the top (an orthogonal cross section orthogonal to the second axis 5B) is to be specified as an active surface.

At this time, the CPU 11 displays images associated with the unit cells 50 selected by the cursor 60 in the image display region 101 of the image viewer 100.

As shown in FIG. 12(C), the time phase (heart rate phase) 32% image is displayed in the center of the image display region 101, the images (time phases 31% and 33%) are displayed at the 1% intervals on the upper and lower sides, and the images (time phases 27% and 37%) are displayed at the 5% intervals on the left and right sides.

When observing images by looking them horizontally, images of the same body-axis direction position can be checked at the time phase 5% intervals such as 26%→31%→36% from the left in the upper row, 27%→32%→37% from the left in the middle row, and 28%→33%→38% from the left in the lower row. Also, when looking images vertically, images of the same body-axis direction position can be checked at the time phase 1% intervals such as 26%→27%→28% from the top in the left column, 31%→32%→33% from the top in the middle column, and 36%→37%→38% from the top in the right column.

Also, the body-axis direction positions of the images displayed in the image display region 101 correspond to the second axis 5B position of the cursor 60 and are all 1.25 mm.

Thus, a number of images can be observed simultaneously by arranging and displaying the images successively from a plurality of viewpoints.

Next, referring to the flow chart in FIG. 13, the flow of image display and retrieval processing in the present first embodiment will be described. Also, in the present embodiment, a case where image display processing is applied for an image for which cardiac-gated scanning and reconstruction are performed will be described.

Figure 13:
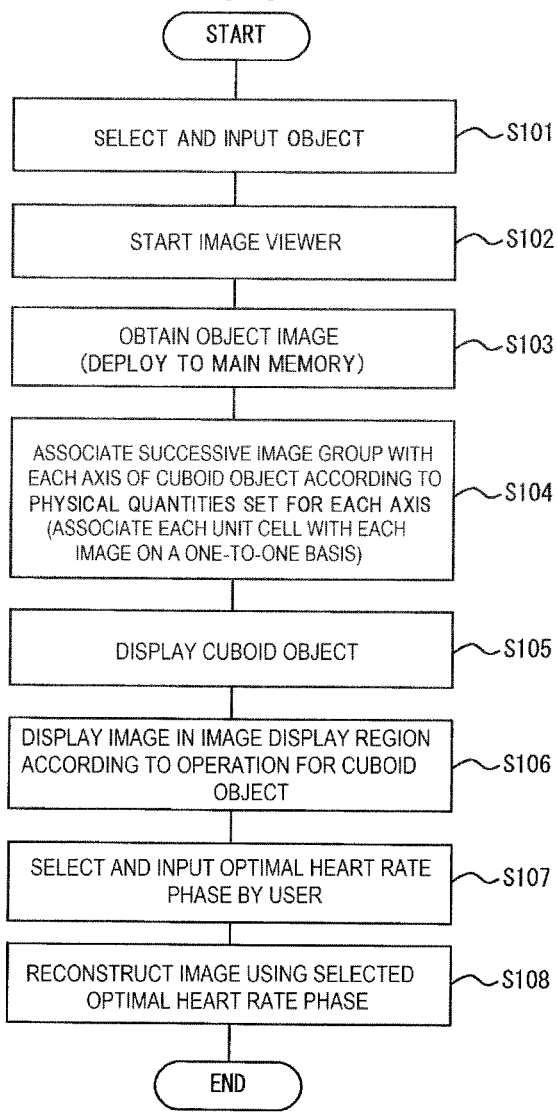
FIG. 13 is an explanatory flow chart for a procedure to select an optimal heart rate phase using the cuboid object 5.

The CPU 11 of the medical image display device 1 retrieves programs and data for image display and retrieval processing of FIG. 13 from the main memory 12 and performs processes based on the programs and data.

Also, when starting the following image display process, cross-sectional imaging data for calculation is to be imported from the image database 3 etc. via the network 2 and the network adapter 14 and is to be stored in the storage device 13 of the medical image display device 1.

First, the CPU 11 displays an input screen to specify an object for observation on the display device 17 and accepts an input of the object by an operator (Step S101). When the targeted object is specified, the CPU 11 retrieves and starts a program for the image viewer 100 from the storage device 13 (Step S102). Also, the CPU 11 obtains an image group of the object specified in Step S101 from the storage device 13 and transmits the image group to the main memory 12 (Step S103).

Then, the CPU 11 generates a successive image group in which the image group obtained in Step S103 is rearranged according to physical quantities specified for the respective axes of the cuboid object 5 and associates the successive image group with the respective axis directions of the cuboid object 5. Hence, the respective unit cells 50 are associated with the respective images included in the successive images on one-to-one basis (Step S104). The CPU 11 displays the cuboid object 5 on the image viewer 100 (Step S105; see FIG. 2).

Next, the CPU 11 accepts operations for the cuboid object 5, changes a display state (an active surface, a cursor position, widths of positioning lines, an axis direction, etc.) of the cuboid object 5 according to the input operation contents, and displays images associated with the unit cells 50 selected by the cursor 60 in the image display region 101 of the image viewer 100 (Step S106). Also, information of the displayed images is displayed in the information display region 102.

The operation details for the cuboid object 5 are, for example, changing an active surface, moving a cursor position, changing widths of row and column lines, changing an axis direction, etc. as described above.

By the image display processing in Step S106, for example, successive images at the time phase 5% intervals and those at the time phase 1% intervals can be arranged and displayed simultaneously, and a body-axis direction position can be switched in order and displayed using a simple operation such as scrolling with a mouse wheel. Hence, because a number of images can be checked simultaneously or successively using a simple operation, an operator can easily retrieve images optimal for observation.

When an image that was judged as an optimal phase by an operator is selected (Step S107), the CPU 11 reconstructs images using projection data of the selected phase and parameters required for diagnosis (Step S108).

According to the above processes, a phase that has less influence of motion artifacts etc. can be displayed and retrieved efficiently among a plurality of successive image groups using the cuboid object 5 provided for the image viewer 100, which makes an operation to search for an optimal heart rate phase easy.

As described above, the medical image display device 1 of the first embodiment displays the cuboid object 5 that is an assembly of a plurality of the unit cells 50 on the display device 17. The medical image display device 1 associates the three axes of the cuboid object 5 with a body-axis direction position, the first time phase intervals (5%), and the second time phase intervals (1%) narrower than the first time phase intervals respectively. The medical image display device 1 arranges images according to physical quantities associated with each axis and generates successive images. Also, the medical image display device 1 associates each image of the successive images with each unit cell 50 on one-to-one basis and memorizes in a main memory. Then, when a three-dimensional position in the cuboid object 5 is specified by an input command from an input device (the mouse 18, the keyboard 19, etc.), the CPU 11 retrieves one or multiple images associated with one or multiple unit cells 50 that is determined by the input three-dimensional position from the main memory 12 and controls so that the images are displayed in the image display region 101.

Therefore, for example, when images that are the most suitable for observation among images groups for which cardiac-gated scanning was performed are selected for each time phase or each body-axis direction position, an optimal image can be selected for each body-axis direction position by simultaneously observing an image group reconstructed at relatively rough R-R time phase intervals and an image group reconstructed at closer R-R time phase intervals. Therefore, desired images can be efficiently retrieved from a number of images before the display.

Also, when a surface switching command is input for the cuboid object 5 to be displayed in the front surface by an input device, the CPU 11 controls so that a surface of the cuboid object 5 to be displayed in the front surface according to the input surface of the cuboid object 5 is switched and displayed. Hence, the front surface of the cuboid object 5 can be switched and displayed according to an observation purpose, which is helpful for an operation to change an active surface.

Also, with an orthogonal cross section orthogonal to any one of the three axes of the cuboid object 5 as an active surface, the CPU 11 displays one or multiple images associated with the respective positions of the active surface in the image display region 101.

Hence, images associated with the respective unit cells of the orthogonal cross section orthogonal to any one of the three axes of the cuboid object 5 can be displayed in the image display region 101 and be observed.

Also, a three-dimensional position in the cuboid object 5 can be input using a positioning line (a row line, column line, or a plate-like object, etc., in this case, the CPU 11 displays the positioning line being overlapped on the cuboid object 5.

Hence, a three-dimensional position in the cuboid object 5 is easily specified and also becomes highly visible.

Also, a positioning line width can be changed, and the CPU 11 controls so that the number of images displayed in the image display region 101 is changed according to the positioning line width.

Hence, the number of images to be collectively displayed in the image display region 101 can be changed freely, which can perform operations efficiently.

Second Embodiment

Next, referring to FIGS. 14 to 17, the second embodiment of the present invention will be described.

Because hardware configuration of the medical image display device 1 in the second embodiment is the same as that in the first embodiment, the repeated explanations will be omitted, and the same section will be described using the same codes.

Although images associated with selected cells on an active surface are to be displayed in the image display region 101 of the image viewer 100 with a cross section (hereinafter, referred to as "orthogonal cross section") orthogonal to any one of the three axes of the cuboid object 5 as an active surface in the first embodiment explanation, the active surface is not limited to the orthogonal cross section but may be a non-orthogonal cross section. The non-orthogonal cross section is a cross section that is not orthogonal to any one of the three axes of the cuboid object 5.

Figure 14:
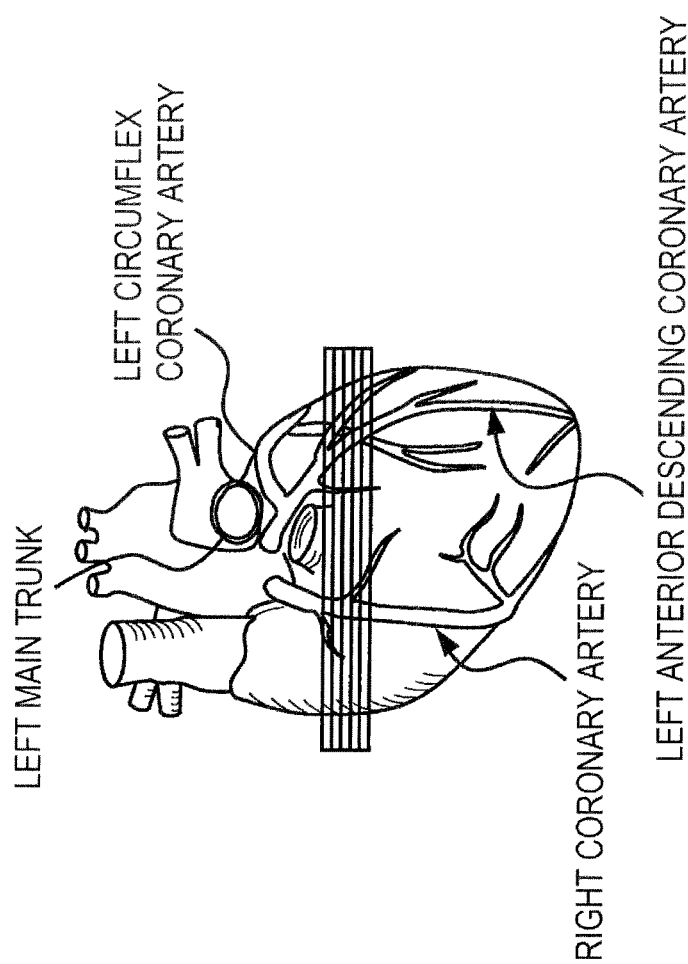
FIG. 14 is an explanatory diagram of observation of the right coronary artery and the left circumflex coronary artery.

For example, when the coronary arteries are evaluated, it is desirable that the most still images (with less motion artifacts) are selected for the two parts of the right coronary artery and left circumflex coronary artery that are most subject to heart rate variability as shown in FIG. 14. However, the diastoles exist in a wide range of the heart rate phases 60% to 95%, and an optimal phase needs to be retrieved in the wide range. Also, an optimal phase is not retrieved only for one cross section and needs to be retrieved also for a plurality of cross-section positions.

Specifically, in the optimal phase search by conventional two-axis image display, an operator first (1) arranges successive images in the order of body-axis directions at the time phase 5% intervals and searches for a phase with less motions of the right coronary artery (RCA) and left circumflex coronary artery (LCA). At this time, for example, it is supposed that both LCA and RCA are satisfactory at the cross-section position "3.75 mm" and the heart rate phase "65%", that only RCA is satisfactory at the cross-section position "5.00 mm" and the heart rate phase "60%", and that only LCA is satisfactory at the cross-section position "2.50 mm" and the heart rate phase "70%". In this case, next, an operator (2) observes successive images arranged in the order of body-axis direction positions around the heart rate phase "60%" that was satisfactory for RCA at the time phase 1% intervals to search for a phase and a cross-section position where RCA is satisfactory.

By the retrieval operation, an optimal phase and a cross-section position of RCA are determined as the cross-section position "5.00 mm" and the heart rate phase "61%". Next, an operator (3) observes successive images in the order of a body-axis direction position at the time phase 1% intervals around the heart rate phase "70%" where LCA was satisfactory to find a phase and a cross-section position where LCA is satisfactory. By the retrieval operation, an optimal phase and a cross-section position of LCA are determined as the cross-section position "2.50 mm" and the heart rate phase "71%". Next, the operator (4) observes successive images in the order of the body-axis direction position at the time phase 1% intervals around the heart rate phase "65%" where both LCA and RCA were satisfactory to find a phase and a cross-section position where both LCA and RCA are satisfactory. By the retrieval operation, an optimal phase and a cross-section position of LCA and RCA are determined as the cross-section position "3.75 mm" and the heart rate phase "66%".

Thus, in case of the conventional two-axis display, at least operations in a total of four stages must be performed.

In case of the above example, when the orthogonal cross section is an active surface as in the first embodiment, image groups at the time phase 5% intervals and those at the time phase 1% intervals can be observed at a time for the same body-axis direction position. However, if simultaneous comparison can be further performed also for a plurality of the body-axis direction positions, the retrieval operation can be performed more efficiently.

Figure 15:
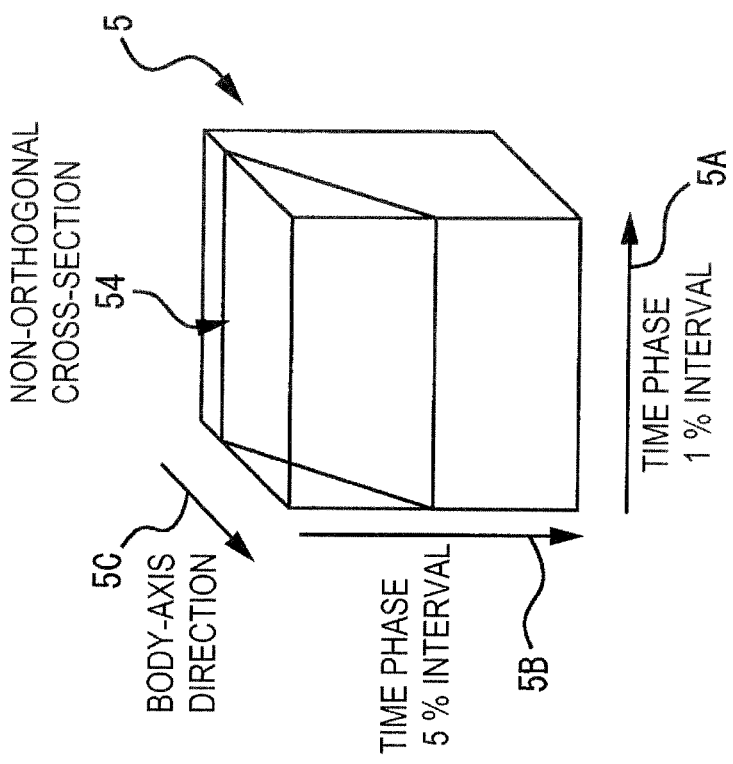
FIG. 15 is an explanatory diagram of a case where the non-orthogonal cross section 54 of the cuboid object 5 is an active surface.

Therefore, the medical image display device 1 in the second embodiment recognizes the non-orthogonal cross section 54 of the cuboid object 5 as an active surface as shown in FIG. 15. In the example of FIG. 15, the cuboid object 5 has the first axis 5A at the time phase 1% intervals, the second axis 5B at the time phase 5% intervals, and the third axis 5C at a body-axis direction position, and the A-B surface 51 is displayed in the front.

As shown in FIG. 16(A), when the cursor 60 is moved by an operator to collectively specify a plurality of the unit cells 50 sterically, the CPU 11 of the medical image display device 1, as shown in FIG. 16(B), diagonally cuts a plurality of the collectively specified unit cell 50 groups and recognizes the unit cells 50 on the non-orthogonal cross section 54 as selected cells. Then, images associated with the selected cells are displayed in the image display region 101 of the image viewer 100. In the example of FIG. 16, a non-orthogonal cross section is a cross section that is parallel to the first axis 5A and non-orthogonal to the second axis 5B and third axis 5C.

Figure 17:
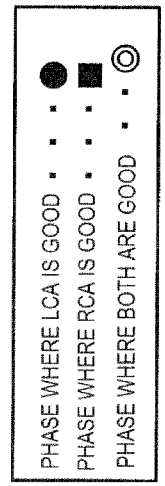
FIG. 17 is an explanatory diagram of an image to be displayed in the image display region 101 when the non-orthogonal cross section 54 is an active surface.

Then, in the image display region 101 of the image viewer 100, a plurality of images are displayed at the body-axis direction position 1.25 mm intervals and the time phase 5% intervals in the vertical direction as well as at the time phase 1% intervals in the horizontal direction as shown in FIG. 17.

An operator can check images of the satisfactory RCA, the satisfactory LCA, or both the satisfactory RCA and satisfactory LCA from the selected images at least one operation of the cursor 60.

As described above, when a non-orthogonal cross section of the cuboid object 5 is recognized an active surface, in a case where there are a plurality of points to be focused, both can be checked simultaneously, resulting in further efficiency improvement.

Third Embodiment

Next, the third embodiment of the medical image display device 1 of the present invention will be described.

In the first and second embodiments, although it was explained that the three axes of the cuboid object are associated with a body-axis direction position, the first time phase intervals (for example, the time phase 5% intervals), the second time phase intervals (for example, the time phase 1% intervals) respectively, physical quantities associated with each axis is not limited to those positions and intervals, and an operator may associate arbitrary physical quantities with them.

In the third embodiment, the medical image display device 1 performs setting processes (hereinafter, referred to as "axis setting processes") of physical quantities for successive image groups to be associated with the three axes of the cuboid object 5. In the axis setting processes, the CPU 11 of the medical image display device 1 displays the axis setting window 200 on the display device 17 and accepts physical quantities input of the successive image groups associated with the respective axes.

Figure 18:
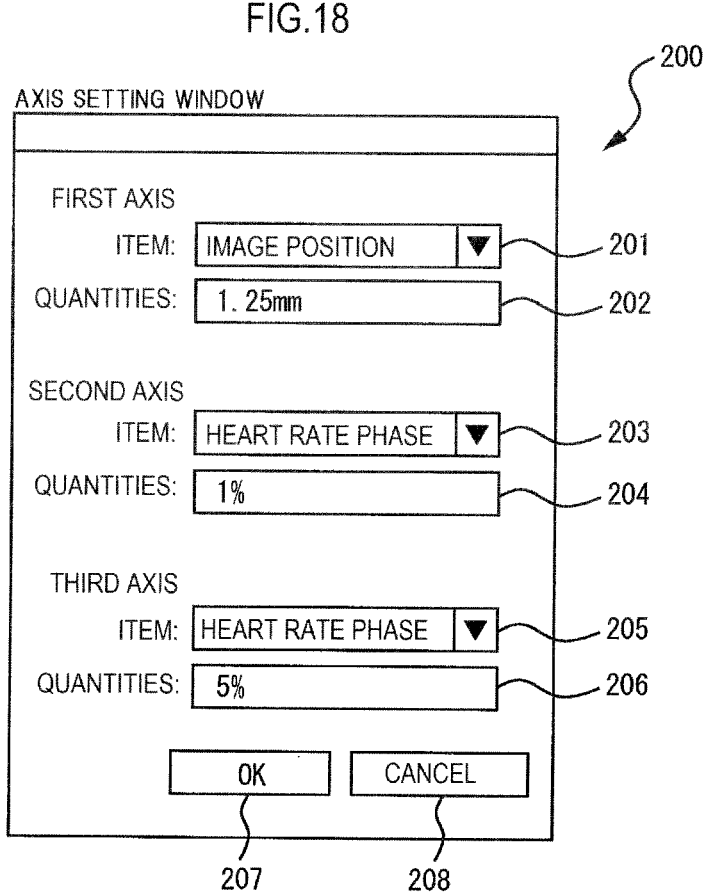
FIG. 18 is an example of the axis setting window 200 for when a setting operation is performed to associate arbitrary physical quantities (item and amount) with each axis of the cuboid object 5.

FIG. 18 is an example of the axis setting window 200.

As shown in FIG. 18, for example, the entry fields 201 to 206 for the items and amounts (intervals) of physical quantities that are respectively associated with the first axis 5A, the second axis 5B, and the third axis 5C of the cuboid object 5 are provided for the axis setting window 200. For example, as in the first embodiment, in case of applying to the optimal heart rate phase search, an operator inputs "IMAGE POSITION" in the item entry field 201 and "1.25 mm" in the amount entry field 202 of the first axis; "HEART RATE PHASE" in the item entry field 203 and "1%" in the amount entry field 204 of the second axis; and "HEART RATE PHASE" in the item entry field 205 and "5%" in the amount entry field 206 of the third axis. Then, the CPU 11 generates the cuboid object 5 where successive images at the body-axis direction position 1.25 mm intervals are associated with the respective unit cells 50 in the first axis direction, successive images at the heart rate phase 1% intervals (time phase 1% intervals) are associated with the respective unit cells 50 in the second axis direction, and successive images at the heart rate phase 5% intervals (time phase 5% intervals) are associated with the respective unit cells 50 in the third axis direction.

The setting item lists for the item entry fields 201, 203, and 205 in the axis setting window 200 may be displayed in a pull-down menu format.

Figure 19:
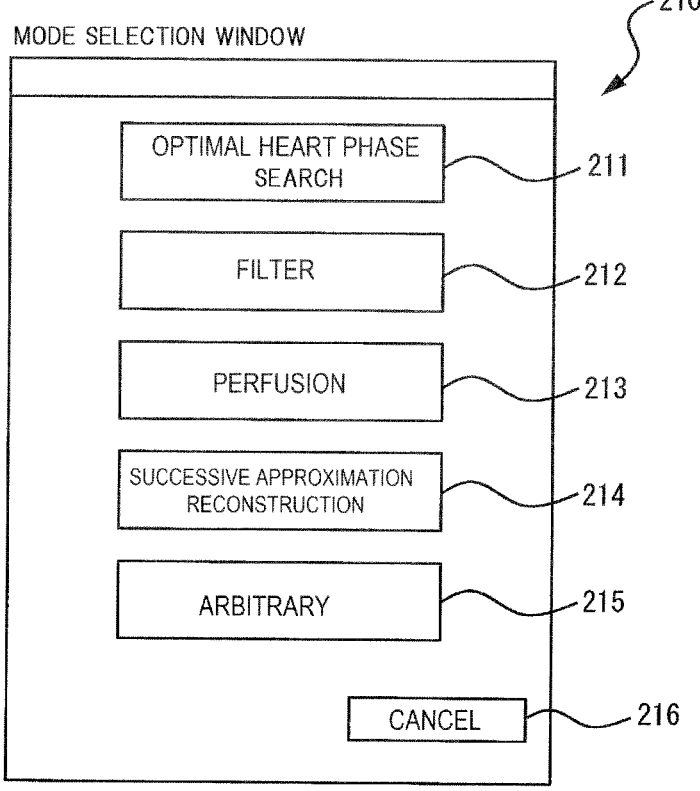
FIG. 19 is an example of the mode selection window 210.

Also, as shown in FIG. 19, a frequently used combination of the axis settings may be maintained to display it as the mode selection window 210 on the display device 17.

In the mode selection window 210 shown in FIG. 19, the respective buttons such as the "optimal heart rate phase SEARCH" mode 211, the "filter" mode 212, the "perfusion" mode 213, the "successive approximation reconstruction" mode 214, and the arbitrary setting mode 215 are displayed.

The "OPTIMAL HEART PHASE SEARCH" mode 211, similarly to the first embodiment, is applied to images for which cardiac-gated scanning was performed and is a mode that associates "body-axis direction position", "first time phase", and "second time phase" with the respective axes of the cuboid object 5.

Figure 20:
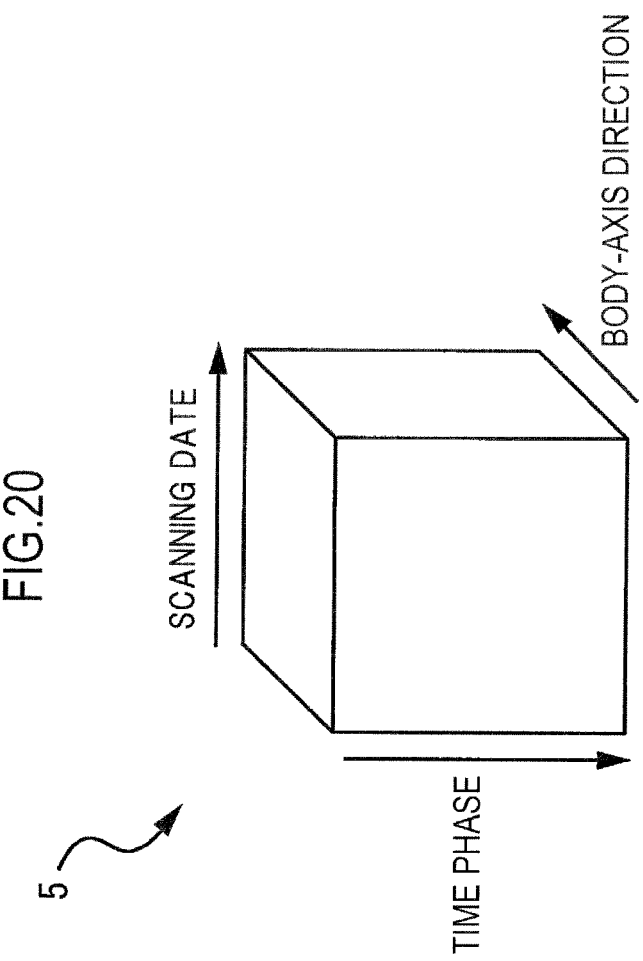
FIG. 20 is an example of physical quantities associated with each axis of the cuboid object 5.

Alternatively, as shown in FIG. 20(A), the "OPTIMAL HEART PHASE SEARCH" mode 211 is applied to images for which cardiac-gated scanning was performed, and "body-axis direction position", "time phase", and "scanning date" may be associated with the respective three axes of the cuboid object 5.

The "FILTER" mode 212 is a mode that is to be applied for when there are multiple groups of filtering processes with different points of view such as a reconstruction filter and image filter. Multiple types of filters included in the respective groups are used in a case such as when arranging images of the respective body-axis direction positions in the order of degree (effectiveness) of the respective filters. For example, the mode is used in a case such as when a repeated adaptive noise reduction process is applied to CT image reconstruction. When the repeated adaptive noise reduction process is applied, as shown in FIG. 21, "IMAGE POSITION", "FIRST FILTER GROUP", and "SECOND FILTER GROUP" are defined as physical quantities of the three axes. In the first filter group and second filter group, multiple types of filters are defined respectively for a site (head, chest, belly, etc.) and a desired image quality (smooth, normal, sharp, etc.). The filters of the first filter group and second filter group have different points of view with each other and can be applied simultaneously.

In the cuboid object 5 of FIG. 21(A), in a case where the surface 53 is an active surface, the CPU 11 displays images in the same body-axis direction position in a horizontal direction in the order of the filter number of the first filter group and in a vertical direction in the order of the filter number of the second filter group as shown in FIG. 21(B). An operator can check effectiveness of the respective filters of both the first filter group and the second filter group for the respective images in the same image position at a time.

Also, in a case where the surface 51 of the cuboid object 5 is an active surface, the CPU 11 displays images of the same filter (for example, "+1" etc.) in the second filter group in a horizontal direction in the order of the filter number of the first filter group and in a vertical direction in the order of the body-axis direction position as shown in FIG. 21(C). An operator can check the respective filters of the second filter group while comparing with effectiveness of the respective filters of the first filter group for each body-axis direction position at a time.

Also, in a case where the surface 52 of the cuboid object 5 is an active surface, the CPU 11 displays images of the same filter (for example, "head normal" etc.) in the first filter group in a horizontal direction in the order of the filter number of the second filter group and in a vertical direction in the order of the body-axis direction position as shown in FIG. 21(D). An operator can check the respective filters of the first filter group while comparing with effectiveness of the filters of the second filter group for each body-axis direction position at a time.

Figure 22:
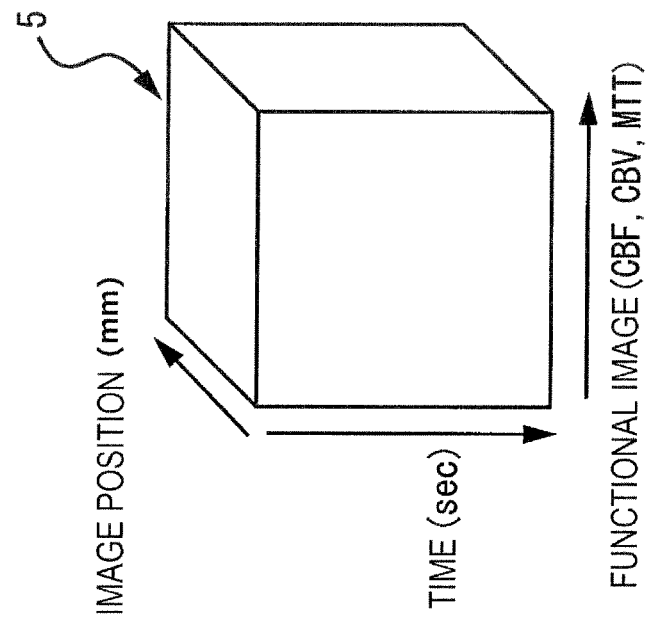
FIG. 22 is an example of physical quantities associated with each axis of the cuboid object 5 in a perfusion mode.

The "PERFUSION" mode 213 is a mode that is applied to image diagnosis (perfusion) to measure a cerebral blood flow using a CT image. In the functional image shown in FIG. 22, CBF means an image showing a cerebral blood flow, CBV means an image showing a cerebral blood volume, and MTT means an image showing a mean transit time of blood. In the "PERFUSION" mode 213, "image position (cross section)", "time", and "functional image type" are associated with the respective axes of the cuboid object 5.

Figure 23:
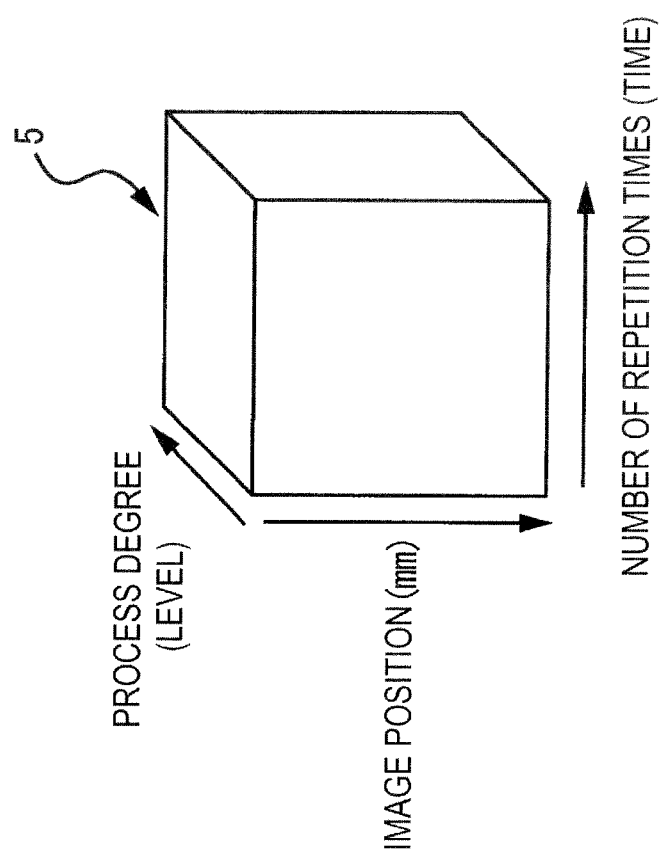
FIG. 23 is an example of physical quantities associated with each axis of the cuboid object 5 in a successive approximation reconstruction mode.

The "SUCCESSIVE APPROXIMATION RECONSTRUCTION" mode 214 is a mode where "the number of times to repeat the process for successive approximation reconstruction", "degree (strength) of the noise reduction process", and "image position" are associated with the respective axes of the cuboid object 5 as shown in FIG. 23.

The arbitrary setting mode 215 is a mode to determine physical quantities set for the respective axes arbitrarily by an operator. The axis setting window 200 shown in FIG. 18 is displayed, and physical quantities of successive images are associated with the respective axes according to the item and amount input arbitrarily on the axis setting window.

By providing the mode selection window 210 shown in FIG. 19, frequently used axis settings can be combined easily.

Figure 24:
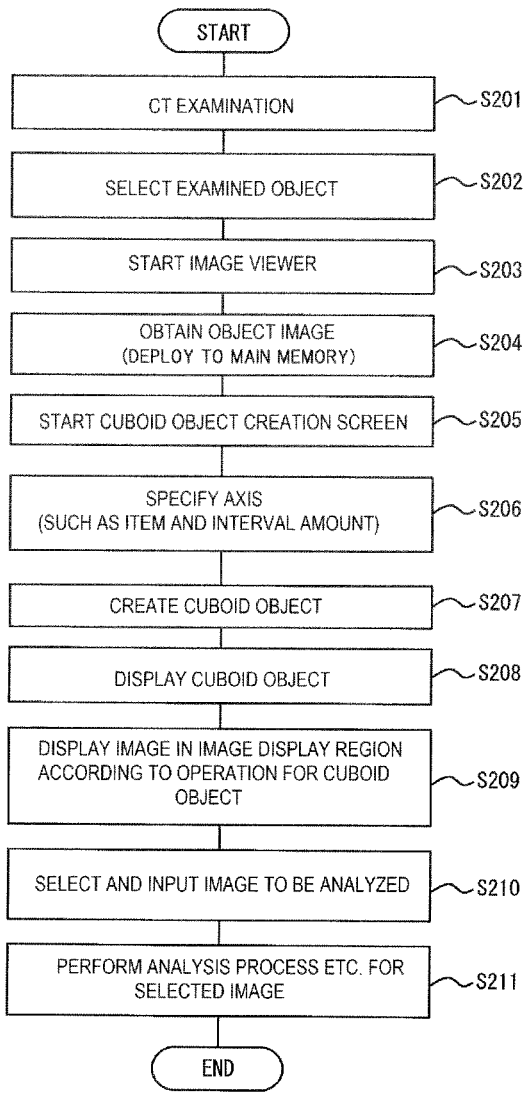
FIG. 24 is an explanatory flow chart for an overall processing procedure for when associating arbitrary physical quantities (item and amount) with each axis of the cuboid object 5.

FIG. 24 is a flow chart to describe a continuous flow from conducting the examination to image analysis.

As shown in FIG. 24, when a CT examination etc. using an X-ray CT apparatus is first conducted, scanned images, object information, etc. are registered in the image database 3 (Step S201).

When an image analysis process etc. is performed in the medical image display device 1, an operator first selects an examined object (Step S202) For example, the CPU 11 should be configured so that it displays an input screen to specify an object for observation on the display device 17 and accepts an object input by an operator. When an object for observation is specified, the CPU 11 retrieves a program for the image viewer 100 from the storage device 13 and starts it (Step S203). The CPU 11 obtains an image group of the object specified in Step S202 from the storage device 13 and transmits it to the main memory 12 (Step S204).

Then, the CPU 11 starts up the cuboid object creation screen (Step S205). The cuboid object creation screen includes, for example, the mode selection window 210 shown in FIG. 19 and the axis setting window 200 shown in FIG. 18.

When a desired mode is selected in the mode selection window 210 or when the axis setting window 200 in an arbitrary mode is started up, the CPU 11 specifies physical quantities set for the respective axis of the cubic project 5 (Step S206).

The CPU 11 creates the cuboid object 5 based on the physical quantities of the respective axes of the cuboid object 5 set in Step S206 (Step S207). That is, the image group obtained in Step S204 based on the physical quantities set for the respective axes of the cuboid object 5 is rearranged, and a successive image group is generated and associated with the respective axis directions of the cuboid object 5. Hence, the respective unit cells 50 and the respective images included in successive images are associated with each other on one-to-one basis (Step S207). The CPU 11 displays the cuboid object 5 on the image viewer 100 (Step sS208).

Next, the CPU 11 accepts operations for the cuboid object 5 and changes a display status (an active surface, a cursor position, a line width and an axis direction of row and column lines) of the cuboid object 5 according to the contents of the input operations as well as displays an image associated with the unit cell 50 selected by the cursor 60 in the image display region 101 of the image viewer 100 (Step S209). Also, information of the displayed image is displayed in the information display region 102.

For example, as described before, the operation contents for the cuboid object 5 are changing an active surface, moving a cursor position, changing a line width of the row and column lines and an axis direction, etc. Orthogonal and non-orthogonal cross sections of the cuboid object 5 may be recognized as an active surface.

When an image that was determined as an analysis target by an operator through the Step S209 process is selected (Step S210), the CPU 11 performs an analysis process, etc. based on the selected image (Step S211).

As described above, arbitrary physical quantities can be associated with the respective axes of the cuboid object 5 by the medical image display device 1 of the third embodiment. This can apply the image retrieval using the cuboid object 5 to various image processes, resulting in the utility improvement.

Although the preferred embodiment of the medical image display device 1 related to the present invention was described, the present invention is not limited to the embodiments described before.

In the above first to third embodiments, a size of the unit cell 50 of the cuboid object 5 or a size of the cuboid object 5 itself may be arbitrarily changed.

As shown in FIG. 25(A), it may be configured so that a size of the unit cells 50 composing the cuboid object 5 is changed according to image information. In a case where a body-axis direction position is set for the third axis 5C of the cuboid object 5, when a side length of the third axis direction of the unit cells 50 is also that according to the image thickness, the image thickness can be easily scanned only by taking a look at the cuboid object 5.

Also, for example, as shown in FIG. 25(B), it may be configured so that a size of the cuboid object 5 itself is changed according to an image amount. In a case where a body-axis direction position is set for the third axis 5C of the cuboid object 5, if there are three images of the same image thickness, the cuboid object 5 of the three unit cells 50 should be created. Additionally, if there are five images of the same image thickness, the cuboid object 5 of the five unit cells 50 should be created.

Also, interval widths of the unit cells 50 of the respective axes may be changed according to the display space of the cuboid object 5. For example, when the display space of the cuboid object 5 is narrow in a vertical direction, the interval widths of the unit cells 50 are widened for a vertical axis. Specifically, an example where time phase intervals of 5% are changed to those of 10%, etc. is given.

Also, in the above first to third embodiments, the display formats of the cuboid object 5 and the image display region 101 of the image viewer 100 may be arbitrarily changed depending on the existence of an image.

For example, as shown in FIG. 26(A), in a case where there are no images to be associated with the unit cells 50 when the respective images are associated with the respective unit cells 50 of the cuboid object 5, colors, patterns, etc. of the unit cells 50 vary between areas with and without images. Also, when a region including the unit cells 50 without images is specified by the cursor 60, blanks should be displayed for the unit cells 50 without images when the CPU 11 displays images of the selected cells in the image display region 101.

Also, as shown in FIG. 26(B), when a move operation is performed for positioning lines (row and column lines) to move the cursor 60 on the cuboid object 5 in a case where the unit cells 50 without images to be associated are included in a row or column of the row or column lines, it may be configured so that colors, patterns, etc. of the row or column lines are changed in the row or column.

Also, the shape of the cuboid object 5 is not limited to a cube, and the other shapes may be available.

For example, a shape with multiple cubes combined, a sphere, and the other three-dimensional shape may be available.

Additionally, it is obvious that a person skilled in the art can conceive of a variety of modifications or alterations within the scope of the technical spirit disclosed in the present application, and it is understood that they are also naturally included in the technical scope of the present invention.

DESCRIPTION OF REFERENCE NUMERALS

1: medical image display device, 11: CPU, 12: main memory, 13: storage device, 14: network adapter, 15: display memory, 16: controller, 17: display device, 18: mouse, 19: keyboard, 2: network, 3: image database, 100: image viewer, 101: image display region, 102: information display region, 5: cuboid object, 5A: first axis, 5B: second axis, 5C: third axis, 51: A-B surface (orthogonal cross section), 52: B-C surface (orthogonal cross section), 53: A-C surface (orthogonal cross section), 61, 64, and 66: positioning line (row line), 62, 63, and 65: positioning line (column line), 71 and 72: plate-like object, 54: non-orthogonal cross section, 55: axis direction rotation GUI, 200: axis setting window, 210: mode selection window

The invention claimed is:

1. A medical image display device that displays medical images, comprising:
   a display unit displaying a cuboid object that is an assembly of multiple unit cells;
   a storage unit memorizing images included in a successive image group and corresponding to respective unit cells, each unit cell of the cuboid object being associated on one-to-one basis with a corresponding image according to predetermined physical quantities for the respective three directions of the three axes of the cuboid object;
   an input unit inputting a three-dimensional position in the cuboid object, and
   a control unit controlling so that one or multiple images associated with one or multiple unit cells determined according to the three-dimensional position input from the input unit are retrieved from the storage unit and are displayed on the display unit,
   wherein the input unit inputs the three-dimensional position in the cuboid object using a positioning line, and
   the control unit controls so that the display unit displays the positioning line superimposed on the cuboid object, and
   wherein the input unit inputs a line width of the positioning line, and
   the control unit controls so that the number of images that the display unit displays is changed according to the line width of the positioning line that is input by the input unit.

2. The medical image display device according to claim 1, wherein the input unit inputs a surface of the cuboid object that the display unit displays in front, and
   the control unit controls so that a surface of the cuboid object which the display unit displays in front is switched and displayed according to the surface of the cuboid object input by the input unit.

3. The medical image display device according to claim 1, wherein the input unit inputs physical quantities of the one or multiple successive image groups to be associated any of the three axes of the cuboid object, and
   the control unit controls so that the successive image groups are changed in which the storage unit memorizes the respective unit cells associated with the successive image groups on one-to-one basis according to the one or multiple physical quantities input by the input unit.

4. The medical image display device according to claim 1, wherein the input unit inputs one or multiple orthogonal cross section orthogonal to any of the three axes of the cuboid object, and
   the control unit controls so that the display unit displays one or multiple images associated with the respective positions of the orthogonal cross section according to the one or multiple orthogonal cross sections input by the input unit.

5. The medical image display device according to claim 1, wherein the input unit inputs one or multiple non-orthogonal cross sections that are not orthogonal to any of the three axes of the cuboid object, and
   the control unit controls so that the display unit displays one or multiple images associated with the respective position of the non-orthogonal cross sections according to the one or multiple non-orthogonal cross sections input by the input unit.

6. The medical image display device according to claim 1, wherein the medical images are those used for the cardiac-gated reconstruction process, and
   the three physical quantities input by the input unit are a position in the body-axis direction, a first time phase interval, and a second time phase interval narrower than the first time phase interval.

7. The medical image display device according to claim 1, wherein the input unit inputs replacement of the vertical axis and the horizontal axis that specifies display positions of the respective images when multiple images are displayed on the display unit, and
   the control unit controls so that the respective images displayed on the display unit are rearranged according to the replacement of the vertical axis and the horizontal axis input by the input unit.

8. The medical image display device according to claim 1, wherein the control unit controls so that colors or patterns of the unit cells vary between areas with and without images associated with the unit cells.

9. The medical image display device according to claim 8, wherein the control unit controls so that blanks are displayed for display positions corresponding to unit cells that are not associated with images when a plurality of images associated with a plurality of unit cells determined according to a three-dimensional position input by the input unit are displayed on the display unit.

10. The medical image display device according to claim 1,
wherein the control unit controls so that colors or patterns of the positioning line superimposed on the cuboid object vary between areas with and without images associated with the unit cells.

11. A medical image display method that a medical image display device displaying medical images performs, including:
 a displaying step where a display unit displays a cuboid object that is an assembly of multiple unit cells;
 a memorizing step where a storage unit memorizes images included in a successive image group and corresponding to respective unit cells, each unit cell of the cuboid object being associated on one-to-one basis with a corresponding image according to a predetermined physical quantities with the respective directions of the three axes of the cuboid object;
 an inputting step where an input unit inputs a three-dimensional position in the cuboid object, and
 a controlling step where a control unit controls so that one or multiple images associated with one or multiple unit cells determined according to the three-dimensional position input from the input unit are retrieved from the storage unit and are displayed on the display unit,
wherein the inputting step inputs the three-dimensional position in the cuboid object using a positioning line, and
the controlling step controls so that the display unit displays the positioning line superimposed on the cuboid object, and
wherein the inputting step inputs a line width of the positioning line, and
the controlling step controls so that the number of images that the display unit displays is changed according to the line width of the positioning line tat is input by the inputting step.

* * * * *